United States Patent
Skarda et al.

(10) Patent No.: US 10,973,566 B2
(45) Date of Patent: *Apr. 13, 2021

(54) SUBXIPHOID CONNECTIVE LESION ABLATION SYSTEM AND METHOD

(71) Applicant: Medtronic, Inc., Minneapolis, MN (US)

(72) Inventors: James Skarda, Lake Elmo, MN (US); Steven Bolling, Ann Arbor, MI (US); Daniel Cheek, Plymouth, MN (US); Brian Ross, Maple Grove, MN (US); Mitchell Strain, St. Paul, MN (US); Steve Ramberg, North Oaks, MN (US); Thomas J Conway, White Bear Lake, MN (US); Randy Thill, St. Paul, MN (US)

(73) Assignee: Medtronic, Inc., Minneapolis, MN (US)

(*) Notice: Subject to any disclaimer, the term of this patent is extended or adjusted under 35 U.S.C. 154(b) by 670 days.

This patent is subject to a terminal disclaimer.

(21) Appl. No.: 15/787,173

(22) Filed: Oct. 18, 2017

(65) Prior Publication Data
US 2018/0049796 A1 Feb. 22, 2018

Related U.S. Application Data

(63) Continuation of application No. 12/769,001, filed on Apr. 28, 2010, now Pat. No. 9,820,803.

(51) Int. Cl.
*A61B 18/14* (2006.01)
*A61B 18/00* (2006.01)
*A61B 18/12* (2006.01)

(52) U.S. Cl.
CPC .... *A61B 18/14* (2013.01); *A61B 2018/00351* (2013.01); *A61B 2018/00363* (2013.01);
(Continued)

(58) Field of Classification Search
CPC .......... A61B 2018/00273; A61B 2018/00291; A61B 2018/00357; A61B 2018/00363; A61B 2018/00351; A61B 2018/1467
See application file for complete search history.

(56) References Cited

U.S. PATENT DOCUMENTS 5,370,671 A 12/1994 Maurer et al.
5,533,958 A 7/1996 Wilk
(Continued)

FOREIGN PATENT DOCUMENTS

WO 2004069069 8/2004

OTHER PUBLICATIONS

International Search Report for PCT/US2011/031618 dated Jun. 28, 2011.
Select prosecution Responses in U.S. Appl. No. 12/769,001.

*Primary Examiner* — Ronald Hupczey, Jr.
(74) *Attorney, Agent, or Firm* — Dicke, Billig & Czaja, PLLC

(57) ABSTRACT

Instrument and systems for applying ablative energy to epicardial tissue via a subxiphoid access surgical approach. The instrument has a head assembly sized and shaped for a subxiphoid surgical approach to a patient's heart and defines a contact face. The head assembly includes a paddle body, a first ablation electrode, and a second ablation electrode. The ablation electrodes are coupled to the paddle body in a spaced apart, spatially-fixed fashion. The ablation electrodes are exteriorly exposed at the contact face. A tubular member extends from the head assembly and maintains wiring connected to the ablation electrodes. The instrument is manipulable to locate the contact face on epicardial tissue of a patient's heart via a subxiphoid surgical approach, such as between the left and right pulmonary vein junctions of the posterior left atrium.

18 Claims, 20 Drawing Sheets

(52) U.S. Cl.
CPC ............ *A61B 2018/00577* (2013.01); *A61B 2018/126* (2013.01); *A61B 2018/1467* (2013.01); *A61B 2018/1497* (2013.01)

(56) References Cited

U.S. PATENT DOCUMENTS

| | | | |
|---|---|---|---|
| 6,035,238 A | 3/2000 | Ingle et al. | |
| 6,063,081 A | 5/2000 | Mulier et al. | |
| 6,228,110 B1 * | 5/2001 | Munsinger | A61F 2/95 604/96.01 |
| 6,238,393 B1 | 5/2001 | Mulier et al. | |
| 6,283,987 B1 | 9/2001 | Laird et al. | |
| 6,290,699 B1 | 9/2001 | Hall et al. | |
| 6,328,736 B1 | 12/2001 | Mulier et al. | |
| 6,432,104 B1 | 8/2002 | Durgin et al. | |
| 6,475,216 B2 | 11/2002 | Mulier et al. | |
| 6,477,396 B1 | 11/2002 | Mest et al. | |
| 6,514,250 B1 * | 2/2003 | Jahns | A61B 18/1492 600/387 |
| 6,515,250 B2 | 2/2003 | Miyasaka et al. | |
| 6,558,382 B2 | 5/2003 | Jahns et al. | |
| 6,584,360 B2 | 6/2003 | Francischelli et al. | |
| 6,706,039 B2 | 3/2004 | Mulier et al. | |
| 6,716,211 B2 | 4/2004 | Mulier et al. | |
| 6,887,238 B2 | 5/2005 | Jahns et al. | |
| 6,960,205 B2 | 11/2005 | Jahns et al. | |
| 6,962,589 B2 | 11/2005 | Mulier et al. | |
| 7,156,845 B2 | 1/2007 | Mulier et al. | |
| 7,261,711 B2 | 8/2007 | Mulier et al. | |
| 7,399,300 B2 * | 7/2008 | Bertolero | A61B 1/12 606/41 |
| 7,487,780 B2 | 2/2009 | Hooven | |
| 7,542,807 B2 | 6/2009 | Bertolero et al. | |
| 7,543,589 B2 | 6/2009 | Hooven | |
| 7,572,257 B2 | 8/2009 | Whayne et al. | |
| 8,439,908 B2 | 5/2013 | Utley et al. | |
| 8,449,449 B2 | 5/2013 | Haarstad et al. | |
| 2003/0032952 A1 | 2/2003 | Hooven | |
| 2003/0135249 A1 | 7/2003 | Laird et al. | |
| 2003/0216725 A1 | 11/2003 | Woloszko et al. | |
| 2004/0111101 A1 | 6/2004 | Chin | |
| 2006/0025756 A1 | 2/2006 | Francischelli et al. | |
| 2006/0025838 A1 | 2/2006 | Laufer et al. | |
| 2007/0156185 A1 | 7/2007 | Swanson et al. | |
| 2008/0161705 A1 | 7/2008 | Podmore et al. | |
| 2008/0243111 A1 | 10/2008 | Gammie et al. | |
| 2009/0163905 A1 | 6/2009 | Winkler et al. | |
| 2009/0299364 A1 | 12/2009 | Batchelor et al. | |
| 2009/0299447 A1 | 12/2009 | Jensen et al. | |
| 2010/0010469 A1 | 1/2010 | Goode et al. | |
| 2010/0081987 A1 | 4/2010 | Christian | |

* cited by examiner

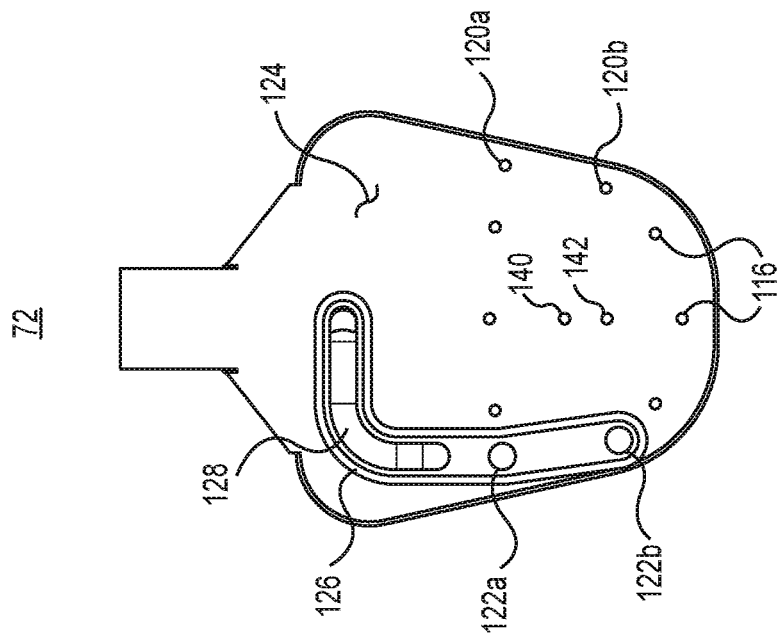
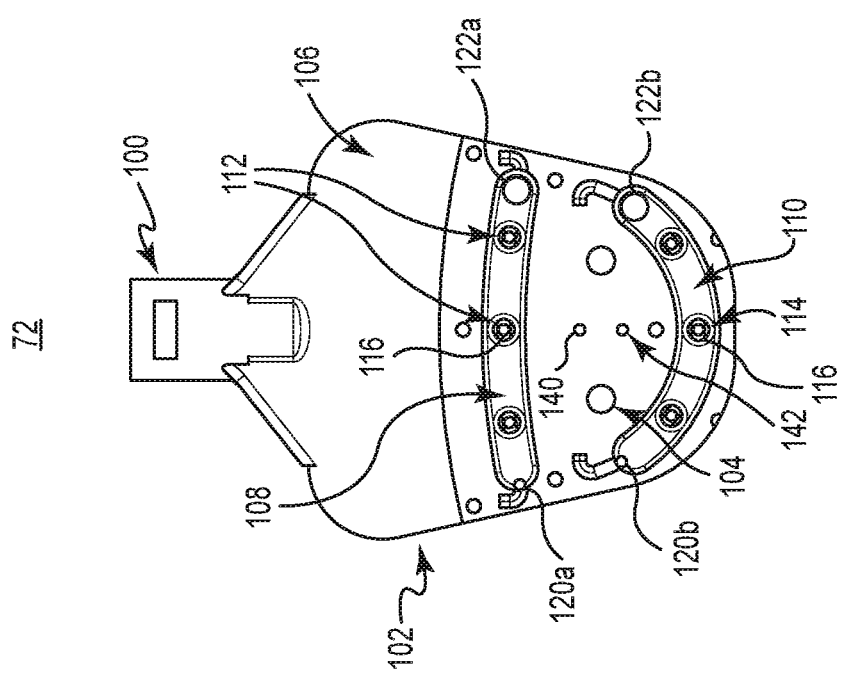

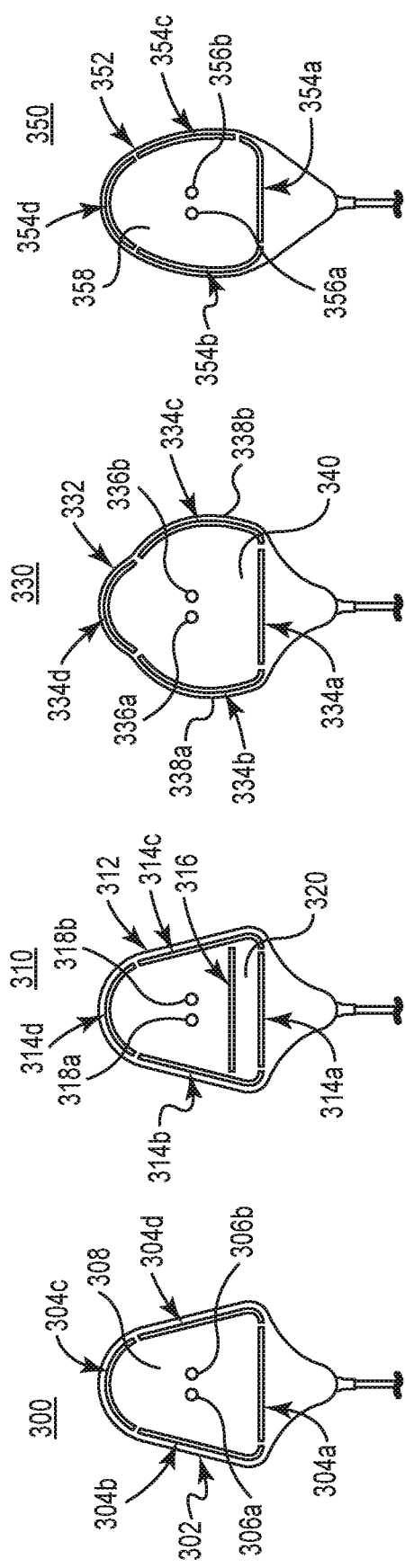

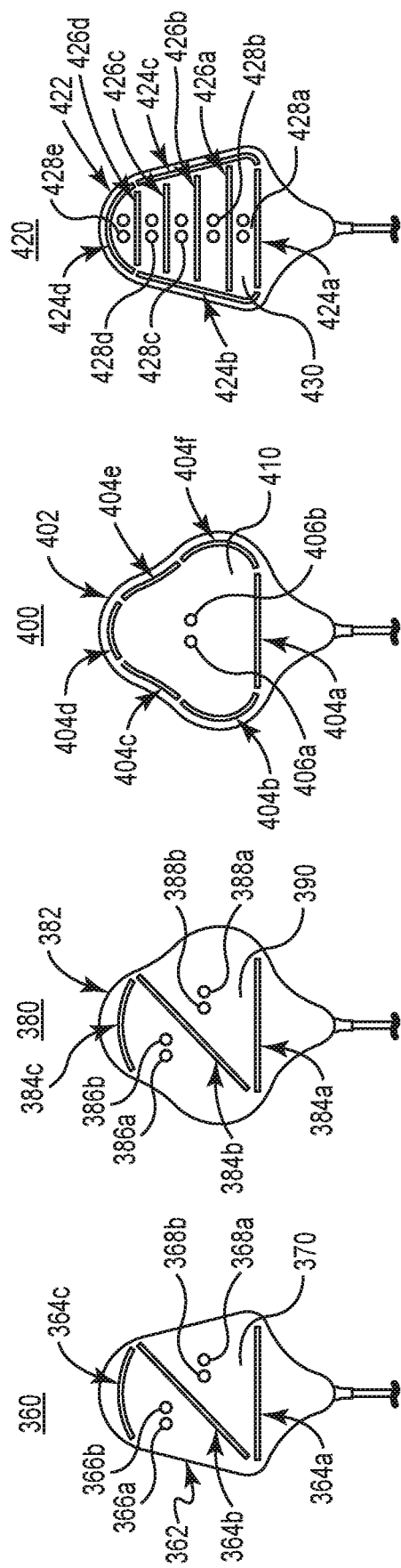

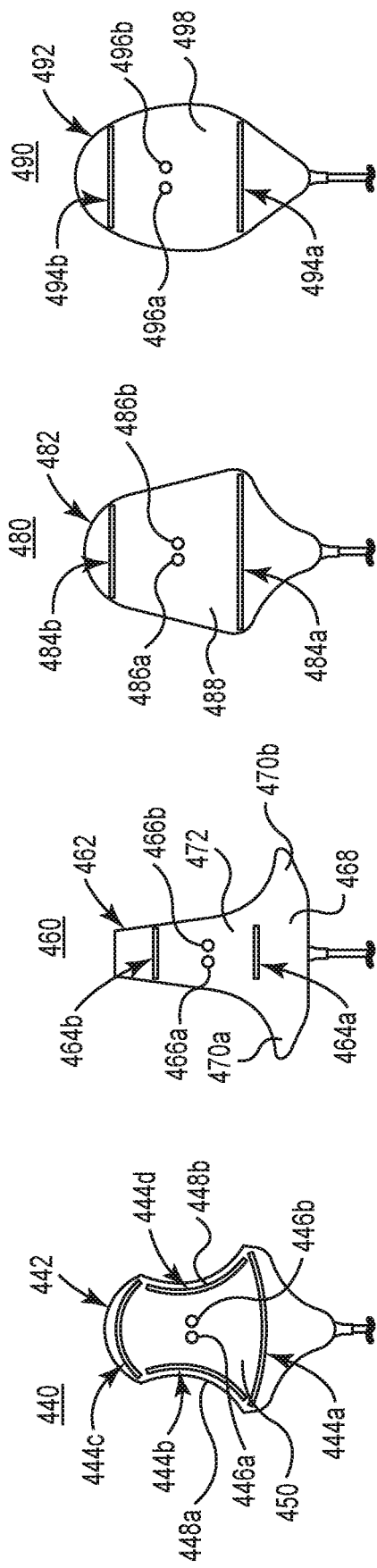

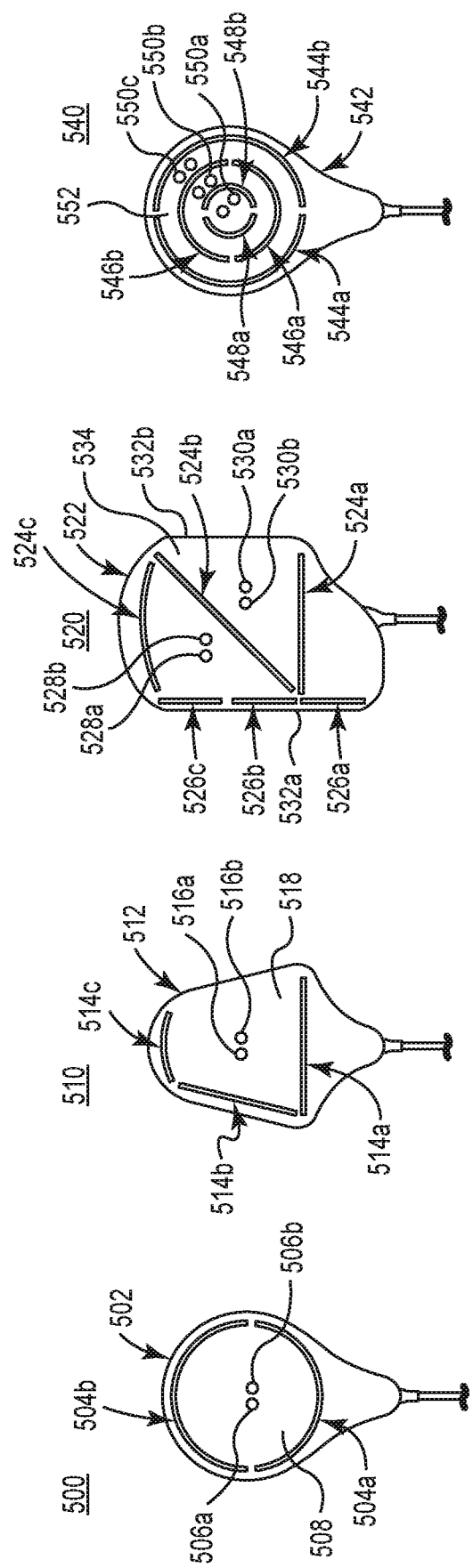

SUBXIPHOID CONNECTIVE LESION ABLATION SYSTEM AND METHOD

CROSS REFERENCE TO RELATED APPLICATION

The present application is a continuation of U.S. Ser. No. 12/769,001, filed Apr. 28, 2010, now allowed, the entire contents of which are fully incorporated herein by reference.

BACKGROUND

Atrial fibrillation is a common cardiac condition in which irregular heart beats cause a decrease in the efficiency of the heart, sometimes due to variances in the electrical conduction system of the heart. In some circumstances, atrial fibrillation poses no immediate threat to the health of the individual suffering from the condition, but may, over time, result in conditions adverse to the health of the patient, including heart failure and stroke. In the case of many individuals suffering from atrial fibrillation, symptoms affecting the patient's quality of life may occur immediately with the onset of the condition, including lack of energy, fainting, and heart palpitations.

In some circumstances, atrial fibrillation may be treated with drugs or through the application of defibrillation shocks. In cases of persistent atrial fibrillation, however, surgery may be required. The surgical procedure originally developed to treat atrial fibrillation is known as a "MAZE" procedure where the atria are surgically cut apart along specific lines and sutured back together. While possibly effective, the MAZE procedure tends to be complex and may require highly invasive access to the thorax. In order to reduce the need to open the atria, thermal ablation tools have been developed to produce lines of inactive tissue along the heart wall that mimic the MAZE procedure. This is most commonly done using radio frequency (RF) ablation devices to ablate and electrically isolate tissue that may be responsible for the improper or electrical conduction that causes atrial fibrillation.

A variety of cardiac ablation devices and methods are currently available for treatment of atrial fibrillation and other arrhythmias. With some systems, endocardial tissue is contacted and ablated, for example via a catheter-based ablation instrument. Conversely, epicardial tissue can be ablated. Conventionally, cardiac surgeons access the epicardial tissue via a standard sternotomy. More recently, certain atrial fibrillation treatment procedures have been advanced that entail ablating small segments of epicardial tissue on a minimally invasive basis, such as via a single or bilateral thoracotomy approach. For example, the junctions of pulmonary veins with the left atrium have been identified as being a common area where atrial fibrillation-triggering foci reside. For many patients, then, atrial fibrillation can be effectively treated by ablating only a portion of the complete MAZE pattern, such as at the pulmonary vein/left atrium junction. More particularly, a viable cardiac arrhythmia treatment technique entails ablating an epicardial lesion into the posterior left atrium around or circumscribing the left pulmonary veins and another epicardial lesion encircling the right pulmonary veins. These island ablation lesions can be formed on a minimally invasive basis via bilateral thoracotomy using clamp-type ablation instruments, for example a surgical ablation device available under the trade name Cardioblate® Gemini™ available from Medtronic, Inc. While well-accepted, the bilateral thoracotomy surgical approach may require the surgeon to perform various additional procedures, such as dissection of pericardial reflections, in order to laterally access the posterior left atrium ablation site(s). Additionally, while the pulmonary vein island ablation represents only a small portion of a complete MAZE procedure, additional epicardial lesions along the left atrium may be beneficial to prevent re-entry of an unwanted sympathetic pathway.

In light of the above, a need exists for systems and methods of making epicardial lesions on selected cardiac locations on a minimally invasive basis, such as along the posterior left atrium via a subxiphoid surgical approach.

SUMMARY

Some aspects in accordance with principles of the present disclosure relate to an ablation instrument for applying ablative energy to epicardial tissue via a subxiphoid access surgical approach to treat cardiac arrhythmia. The ablation instrument includes a head assembly, a tubular member, and wiring. The head assembly is sized and shaped for a subxiphoid surgical approach to a patient's heart and defines a contact face. Further, the head assembly includes a paddle body, a first elongated ablation electrode, and a second elongated ablation electrode. The paddle body defines an outer perimeter of the head assembly. The first and second ablation electrodes are coupled to the paddle body in a spaced apart, electrically isolated fashion such that a spatial relationship between the ablation electrodes is fixed. The ablation electrodes are exteriorly exposed at the contact face of the head assembly, and are maintained entirely within the outer perimeter. The tubular member extends from the head assembly. The wiring is electrically connected to the first and second ablation electrodes for delivering ablative energy thereto, and extends through the tubular member. With this construction, the ablation instrument is manipulatable to locate the contact face at epicardial tissue of a patient's heart via a subxiphoid surgical approach. For example, the ablation electrodes can be located on epicardial tissue of the posterior left atrium between the left and right pulmonary vein junctions via a subxiphoid surgical approach. In some embodiments, the head assembly further include one or more auxiliary electrodes maintained between the ablation electrodes and available for performing various pacing and/or sensing procedures. In other embodiments, the paddle body forms suction regions about each of the ablation electrodes. In other, possibly related embodiments, the head assembly incorporation irrigation delivery features for supplying an irrigation liquid (e.g., saline) that effectuates cooling of the ablation electrodes; the so-delivered liquid can then be evacuated from the head assembly through the suction regions.

Yet other aspects of the present disclosure relate to an ablation system for applying ablative energy to epicardial tissue via a subxiphoid access surgical approach to treat cardiac arrhythmia. The ablation system includes the ablation instrument as described above and a power source for providing ablative energy to the ablation electrodes. In some constructions, the system further includes a controller electronically connected to auxiliary electrodes carried by the paddle body, with the controller being programmed to perform pacing and sensing procedures via the auxiliary electrodes to evaluate effectiveness of a conductive block lesion pattern.

Yet other aspects in accordance with principles of the present disclosure relate to a method for ablating epicardial tissue of a patient to treat cardiac arrhythmia. The method includes inserting an ablation head assembly of an ablation instrument through a subxiphoid access incision in a chest of the patient. The head assembly defines a contact face and includes a paddle body and two elongated ablation electrodes. The ablation electrodes are coupled to the paddle body in a spaced apart, electrically isolated fashion such that a spatial relationship between the first and second ablation electrodes is fixed. The ablation electrodes are exteriorly exposed relative to the contact face and entirely within an outer perimeter defined by the paddle body. Following subxiphoid insertion, the head assembly is directed to bring the ablation electrodes into contact with the epicardial tissue. Ablation energy is then applied to the heart tissue via the ablation electrodes to destroy one or more conduction pathways in the heart. In some embodiments, the method is performed as part of a partial MAZE procedure in which first and second island lesion ablation patterns are formed about junctions of the right pulmonary veins and the left pulmonary veins with the left atrium of the patient's heart. With this in mind, the ablation lesions formed by the ablation electrodes interconnect the island lesions in forming a conductive block along the posterior left atrium. In other embodiments, conductive block testing is performed via the head assembly immediately following the formation of the connective lesions.

BRIEF DESCRIPTION OF THE DRAWINGS

FIG. 6A is a top plan view of a head component of the head assembly of FIG. 5;

FIG. 6B is a bottom plan view of the head component of FIG. 6A;

FIGS. 11A-11R are simplified plan views of other head assemblies in accordance with the present disclosure and useful with the ablation instrument of FIG. 2.

DETAILED DESCRIPTION

Figure 1:
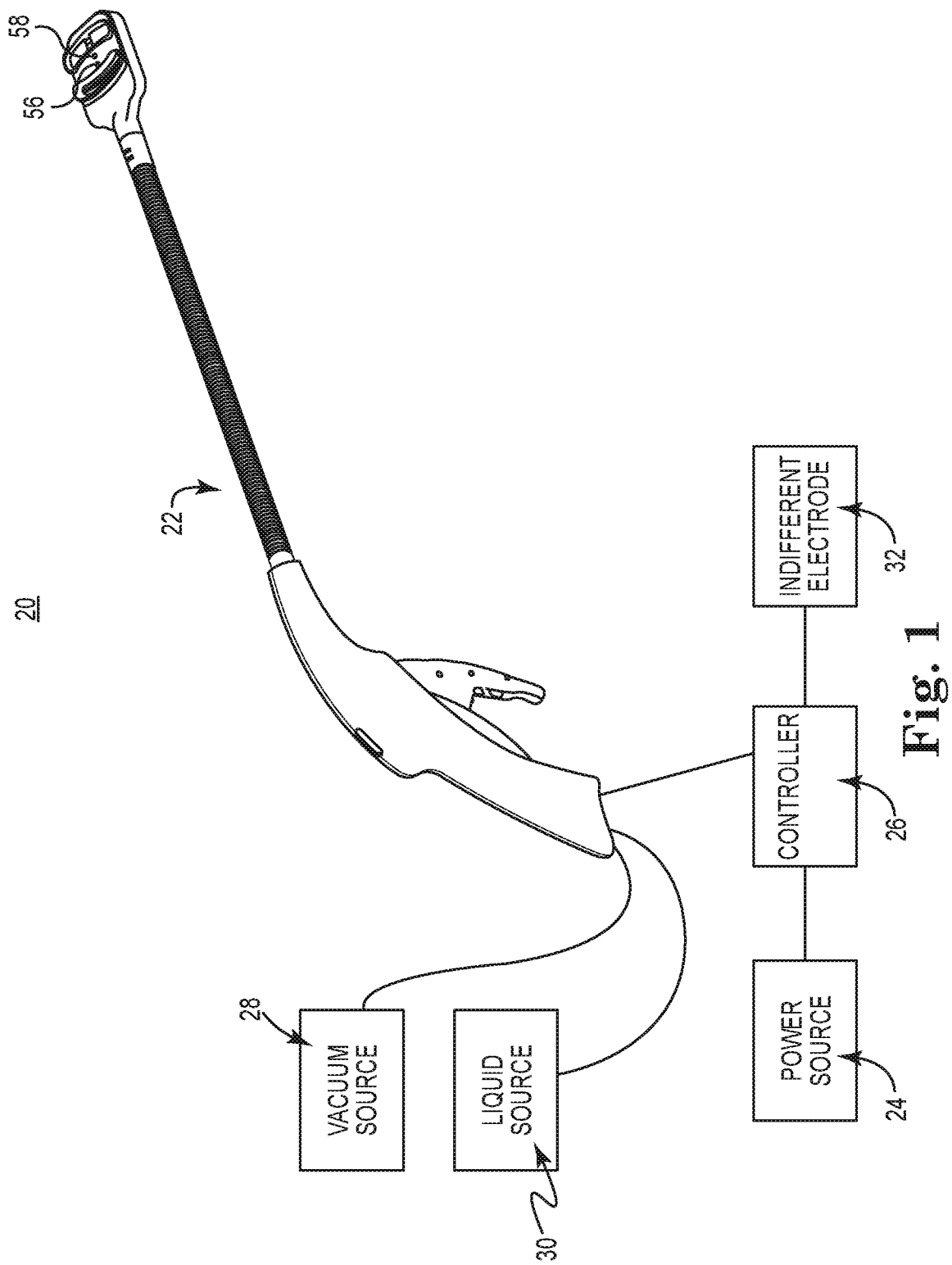
FIG. 1 is a perspective view, with portions shown in block form, of an ablation system useful for applying ablative energy to epicardial tissue via a subxiphoid surgical approach in accordance with principles of the present disclosure.

One embodiment of an ablation system 20 in accordance with aspects of the present disclosure and useful for applying ablative energy to epicardial tissue via a subxiphoid surgical approach is shown in FIG. 1. The ablation system 20 includes an ablation instrument 22 and a power source 24. Optionally, additional components can be provided with the ablation system 20, such as a controller 26 (provided with or apart from the power source 24), a vacuum or negative pressure source 28, a liquid source 30, and an indifferent or grounding electrode 32. Details on the various components are provided below. In general terms, however, the instrument 22 includes a head assembly 40 sized and shaped for accessing epicardial tissue of a patient's heart (e.g., along the posterior left atrium between the left and right pulmonary veins junctions) via a subxiphoid incision in the patient's chest. The head assembly 40 carries various electrodes that, when energized via the power source 24, ablate contacted cardiac tissue to form a corresponding, desired lesion pattern. The controller 26 optionally facilitates performance of various testing procedures with the head assembly 40, such as pace/sense protocols. The optional vacuum source 28 can be employed to draw tissue into more intimate contact with the electrodes carried by the head assembly 40, whereas the optional liquid source 30 can facilitate cooling of the head assembly 40. Regardless, the ablation system 20, and in particular the instrument 22, can be employed on a minimally invasive basis via a subxiphoid surgical approach, uniquely serving to complete a portion of a MAZE lesion pattern, such as interconnecting or otherwise completing a conduction block between island lesion patterns formed on the posterior left atrium about the left and right pulmonary veins.

Figure 2:
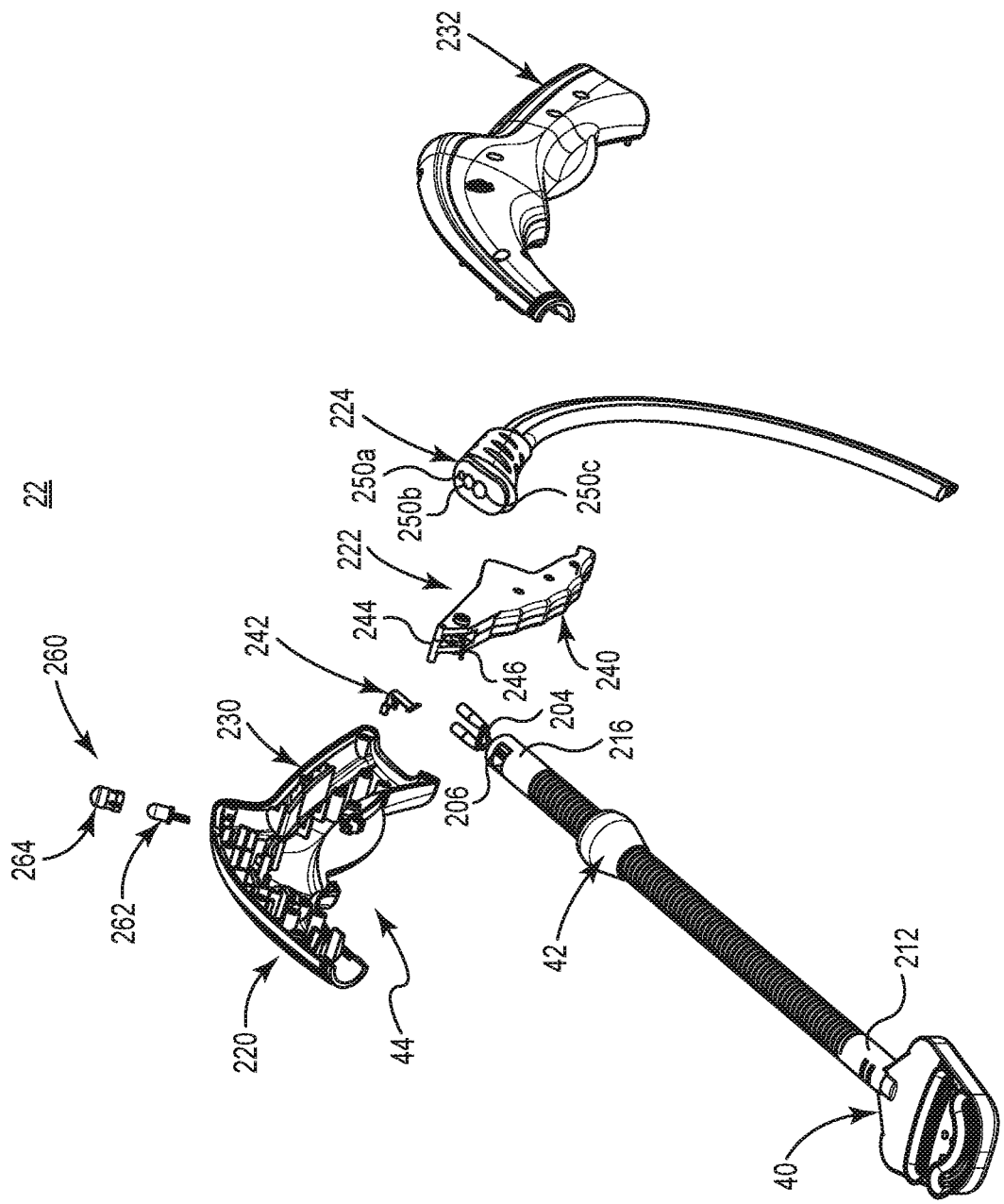
FIG. 2 is an exploded, perspective view of a surgical instrument component of the system of FIG. 1.

With additional reference to FIG. 2, the ablation instrument 22 includes the head assembly 40, a tubular member 42, and a handle assembly 44 (referenced generally). The tubular member 42 supportively connects the head assembly 40 with the handle assembly 44, and provides a protective conduit for wiring and tubing or similar structures (e.g., a suction tube, liquid tube, etc.), to and from the head assembly 40. The handle assembly 44, in turn, promotes handling and operation of the instrument 22, including connecting the instrument 22 with the power source 24 (FIG. 1) and facilitating user control over various operations (e.g., delivery of negative pressure and/or cooling liquid to the head assembly 40).

Figure 3:
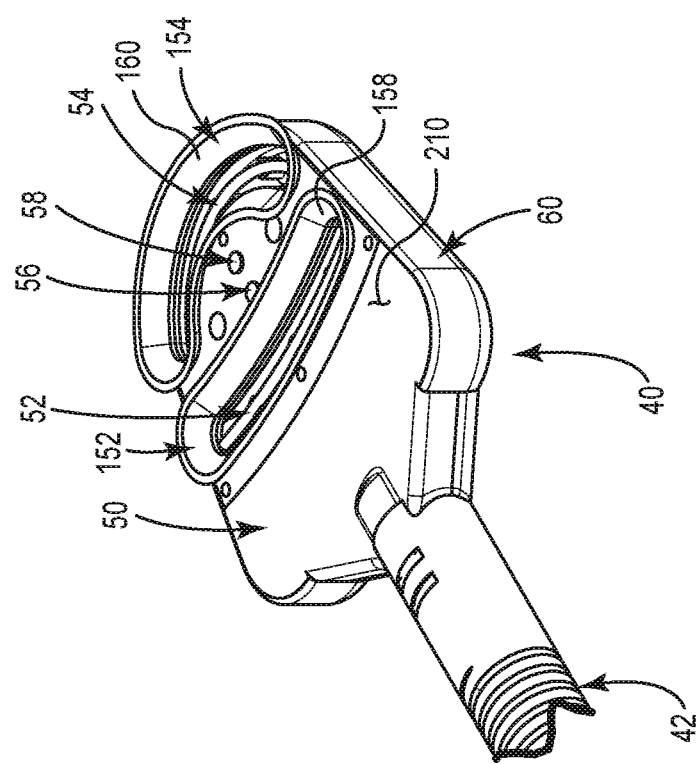
FIG. 3 is an enlarged, perspective view of a head assembly portion of the instrument of FIG. 2.

The head assembly 40 is shown in greater detail in FIG. 3, and generally includes a paddle body 50, a first elongated ablation electrode 52, and a second elongated ablation electrode 54. The ablation electrodes 52, 54 are mounted to the paddle body 50 in a spaced apart, fixed manner, with the paddle body 50 optionally forming suction regions or pods about the ablation electrodes 52, 54, respectively. The paddle body 50 can maintain additional components, such as cooling liquid delivery tubing and/or first and second auxiliary electrodes 56, 58 (e.g., for performing pacing and/or sensing procedures as described below).

The paddle body 50 can assume various forms conducive to subxiphoid insertion and for maintaining the ablation electrodes 52, 54. In more general terms, and as reflected in FIG. 4, the paddle body 50 defines an outer perimeter 60 of the head assembly 40, including a leading end 62, a trailing end 64, and opposing sides 66, 68. Connection of the head assembly 40 with the tubular member 42 (FIG. 2) is provided at the trailing end 64, with the leading end 62 serving as a distal-most end of the instrument 22 (FIG. 2). The leading and trailing ends 62, 64 combine to define a length L of the head assembly 40. The opposing sides 66, 68 combine to define a maximum width W of the head assembly 60. With these designations in mind, a shape of the outer perimeter 60, as well as dimensions of the length L and the maximum width W are sized for subxiphoid insertion, as well as, in some embodiments, to nest between the left and right pulmonary veins at the epicardial surface of the posterior left atrium of an adult human heart. As made clear below, a width of the paddle body 50 is a function of the lengths of the ablation electrodes 52, 54, with these lengths being selected, in some embodiments, to traverse the lateral distance between the junction of the left pulmonary veins with the left atrium and the junction of the right pulmonary veins with left atrium at superior and inferior locations. With these embodiments, then, a width of the paddle body 50 generally coincides with the typical left atrium pulmonary vein junction spacing. Other procedures, and thus other shapes and/or sizes, are also envisioned. While the paddle body 50 is reflected as having a generally trapezoidal perimeter shape, other configurations are also acceptable. For example, while the paddle body 50 is shown as tapering in width from the trailing end 64 to the leading end 62, other shapes are also envisioned (e.g., a more rectangular shape, circular shape, etc.). Regardless, to promote subxiphoid insertion in combination with spanning the pulmonary vein junction distance at the left atrium of a typical adult human heart, the maximum width W of the paddle body 50 can be in the range of 3-7 cm, and the length L can be in the range of 4-12 cm.

Figure 5:
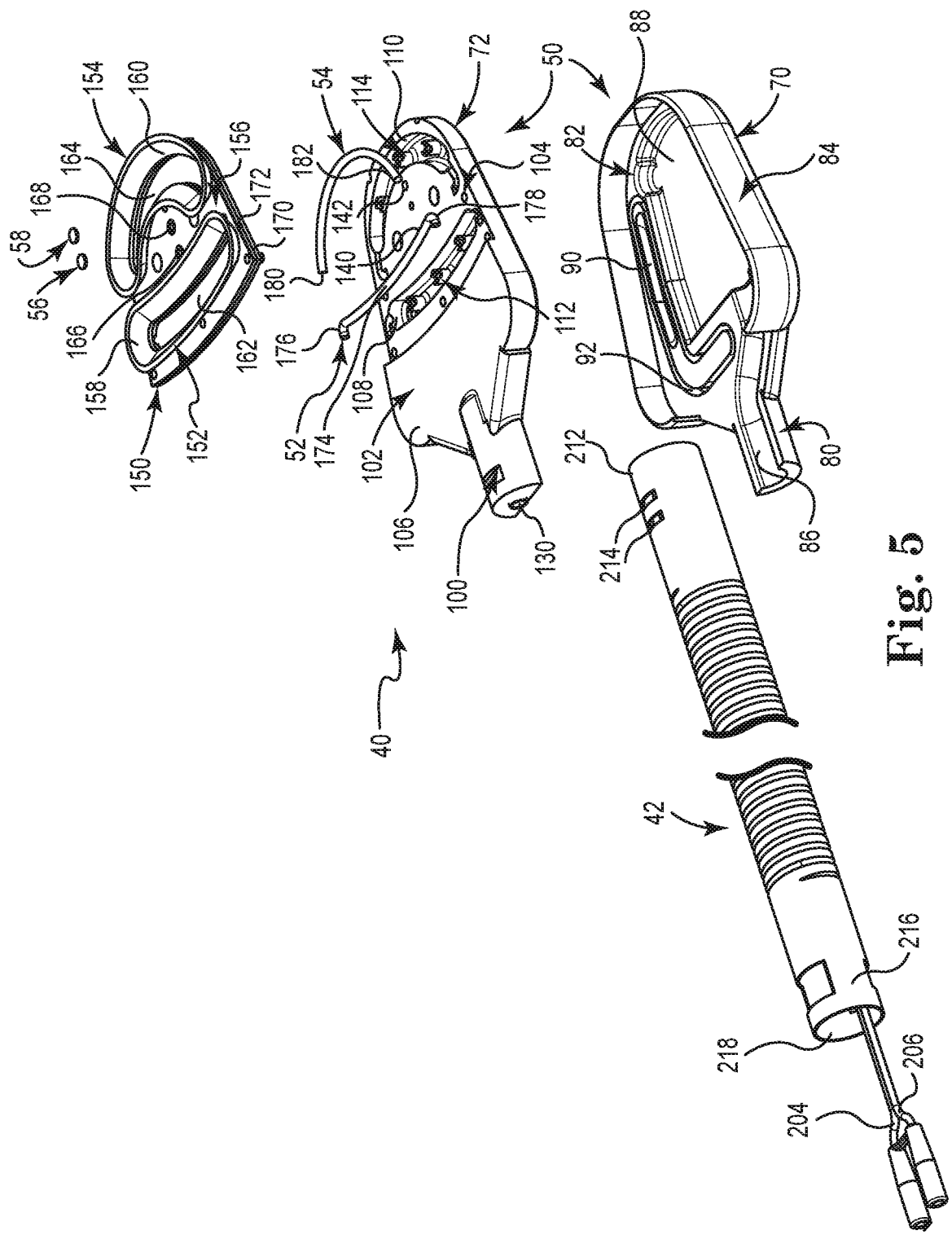
FIG. 5 is an exploded, perspective view of the head assembly of FIG. 3, along with other components of the instrument of FIG. 2.

The paddle body 50 can be constructed as a single, homogeneous piece. Alternatively, a mere complex assembly can be utilized. For example, FIG. 5 illustrates that in some embodiments, the paddle body 50 includes a base 70 and a head 72. With this but one acceptable construction, the head 72 is sized and shaped for assembly to the base 70, with the head 72 providing various features adapted for mounting of the ablation electrodes 52, 54 as described below.

The base 70 can include or define a neck region 80, a floor 82, and a sidewall 84. A trough 86 is formed along the neck region 80 and extends to a chamber 88 formed in the floor 82. The trough 86 and the chamber 88 provide an isolated pathway for various wires and/or tubes upon assembly of the head 72 to the base 70. A suction channel 90 is also formed in the floor 82, and provides a sealed passageway for application negative pressure upon final assembly. In this regard, a track 92 can be formed in the floor 82 about the suction channel 90 and configured to sealingly receive a corresponding feature (e.g., a similarly shaped rib) provided with the head 72. Other assembly configurations are also acceptable that may or may not include the track 92. Finally, the sidewall 84 projects from an outer perimeter of the floor 82, serving to define the outer perimeter 60 (FIG. 4) of the paddle body 50. The base 70 can be formed from various surgically safe materials, and in some embodiments is a molded material that is free of sharp corners for atraumatic insertion into the human body. For example, the base 70 can be a relatively soft polymer such as 72 Durometer urethane. A wide variety of other surgically safe materials (e.g., metals) are also acceptable.

The head 72 can include a neck region 100 and a platform 102. The neck region 100 is sized for mating with the neck region 80 of the base 70. Similarly, the platform 102 is sized and shaped for assembly to the floor 82, nesting within the sidewall 84. In some constructions, the platform 102 defines a leading segment 104 and a trailing segment 106. As shown, the leading segment 104 can be recessed below the trailing segment 106 (relative to the orientation of FIG. 5). Regardless, the leading segment 104 forms a first slot 108 and a second slot 110. With additional reference to FIG. 6A, the first slot 108 is generally sized and shaped in accordance with (e.g., slightly larger than) the first ablation electrode 52, whereas the second slot 110 is sized and shaped to receive the second ablation electrode 54. To facilitate mounting of the ablation electrodes 52, 54 within the respective slots 108, 110, the leading segment 104 can include or form one or more fingers 112, 114 within each of the slots 108, 110, with the fingers 112, 114 being configured to receive and support a segment of the corresponding ablation electrode 52, 54. In some constructions, the fingers 112, 114 are adapted to frictionally retain the corresponding ablation electrode 52, 54 (e.g., press-fit mounting), although other mounting techniques are also envisioned (e.g., adhesive bond). With the but one acceptable construction of FIG. 6A, one or more of the fingers 112, 114 associated with each of the slots 108, 110 can form a longitudinal through hole (referenced generally at 116 for one of the fingers 112 of the first slot 108 and for one of the fingers 114 of the second slot 110) that facilitates the passage of wiring from the corresponding ablation electrode 52 or 54 as described below.

An irrigation hole 120a and/or a suction aperture 122a can optionally be formed in the leading segment 104, fluidly open to the first slot 108; a similar irrigation hole 120b and/or suction aperture 122b can be formed in, and fluidly open to, the second slot 110. Where provided, the irrigation holes 120a, 120b provide a passageway for a liquid delivery tube (not shown) into the corresponding slot 108, 110. The optional suction apertures 122a, 122b fluidly connect a negative pressure source to the corresponding slot 108, 110. For example, as best shown in FIG. 6B, the suction apertures 122a, 122b are fluidly open to a rear face 124 of the head 72. A rib 126 projects from the rear face 124, and surrounds the suction apertures 122a, 122b, as well as a channel 128. The rib 126 is sized to be received within the track 92 (FIG. 5) of the base 70 (FIG. 5), with the channel 128 being fluidly connected to a bore 130 (hidden in FIG. 6B, but shown generally in FIG. 5) in a thickness of the neck region 100. Upon assembly of the base 70 and the head 72 and connection of vacuum tubing (not shown) to the bore 130, negative pressure (e.g., generated by the vacuum source 30 (FIG. 1)) through the bore 130 is applied to the channel 128 of the head 72. The suction channel 90 (FIG. 5) of the base 70 is fluidly connected to the suction channel 128 of the head 72, as well with the suction apertures 122a, 122b, thereby delivering negative pressure to the slots 108, 110 (FIG. 6A). Assembly of the rib 126 within the track 92 fluidly isolates the negative pressure pathway.

Returning to FIGS. 5 and 6A, in some embodiments, the head 72 is further adapted to receive one or more other components in addition to the ablation electrodes 52, 54. For example, with embodiments in which the optional auxiliary electrodes 56, 58 are provided, the leading segment 104 can further form or define first and second auxiliary holes 140, 142. The holes 140, 142 are generally configured to facilitate passage of wiring (not shown) extending from the corresponding auxiliary electrodes 56, 58, and serve to desirably locate the auxiliary electrodes 56, 58 relative to the ablation electrodes 52, 54 upon final assembly. In particular, and for reasons made clear below, the auxiliary electrodes 56, 58 are positioned between the first and second ablation electrodes 52, 54 and at a sufficient distance relative to one another to perform desired operations, such as pacing and/or sensing.

With specific reference to FIG. 5, the paddle body 50 can further include, in some constructions, an optional tissue contact member 150 that is mounted to the leading segment 104 of the head 72. The tissue contact member 150 is generally constructed for atraumatic interface with cardiac tissue, and forms or defines a first skirt 152 and a second skirt 154. The skirts 152, 154 project upwardly from a panel 156 (relative to the orientation of FIG. 5), with the first skirt 152 being generally sized and shaped in accordance with the first ablation electrode 52, and the second skirt 154 being generally sized and shaped in accordance with the second ablation electrode 54. As described below, the skirts 152, 154 establish suction regions or pods 158, 160 relative to the corresponding ablation electrodes 52, 54, with the panel 156 forming openings 162, 164 through a thickness thereof and through which negative pressure established at the first and second suction apertures 122a, 122b (FIG. 6A), respectively, is conveyed to the suction regions 158, 160. With configurations in which the auxiliary electrodes 56, 58 are provided, the tissue contact member 150 forms or defines first and second auxiliary openings 166, 168 configured to maintain a corresponding one of the auxiliary electrodes 56, 58.

In some constructions, the tissue contact member 150 is formed by a first, support layer 170 and a second, skirt layer 172. The support layer 170 generally reinforces the tissue contact member 150, and can be formed of a relatively stiffer material than that of the skirt layer 172. The skirt layer 172 can be over-molded to the support layer 170, and defines the first and second skirts 152, 154. For example, in some embodiments, the support layer 170 is a 72 Durometer urethane material, whereas the skirt layer 152 is a 42 Durometer polyurethane material. Other materials and/or constructions are also acceptable. In yet other embodiments, one or both of the skirts 152, 154 can be integrally formed or defined by the head 72. Where provided, the skirts 152, 154 can be compliant or resiliently deflectable at expected negative pressure levels (e.g., in the range of −100 mm Hg to −400 mm Hg) to promote atraumatic interface with contacted cardiac tissue. That is to say, the skirts 152, 154 will somewhat collapse (e.g., elastically) in the presence of expected negative pressure levels to ensure consistent, intimate contact of the tissue to be ablated with the corresponding ablation electrode 52, 54, In yet other embodiments, one or both of the skirts 152, 154 can be omitted.

The first ablation electrode 52 can assume various forms appropriate for delivering RF energy at sufficient levels for ablating contacted epicardial tissue. For example, the first ablation electrode 52 can be an electrically conductive metal such as 304 stainless steel. In some embodiments, the first ablation electrode 52 is a solid shaft or wire; in other embodiments a tubular construction can be employed. Regardless, the first ablation electrode 52 is generally elongated (e.g., having a longitudinal length at least three times greater than a width or diameter thereof), and can have a slight curvature along an intermediate segment 174 thereof. Further, opposing ends 176, 178 of the first ablation electrode 52 can extend inwardly relative to the intermediate segment 174 as shown. Other shapes are also acceptable. One or more sensing-type components (e.g., thermocouple, transistor, etc.) can optionally be assembled to or formed by the first ablation electrode 52. For example, separate thermocouples (not shown) are provided at each of the ends 176, 178.

The second ablation electrode 54 is constructed of materials similar to those described above with respect to the first ablation electrode 54, and in some embodiments is a solid metal wire or shaft. With the but one acceptable construction of FIG. 5, the second ablation electrode 54 is generally elongated, having a relatively continuous, planar curve extending between opposing ends 180, 182 and defining a radius of curvature that is less than that of the intermediate segment 174 of the first ablation electrode 52. Other shapes are also envisioned. For example, the ablation electrodes 52, 54 can have identical shapes. Regardless, one or more sensing elements (e.g., thermocouple, transistor, etc.) can be provided with the second ablation electrode 54, for example at one or both of the ends 180, 182.

The optional auxiliary electrodes 56, 58 can be identical, and can assume any conventional form appropriate for performing the pacing and/or sensing protocols described below. Thus, the auxiliary electrodes 56, 58 can be electrically conductive metal buttons.

Figure 7:
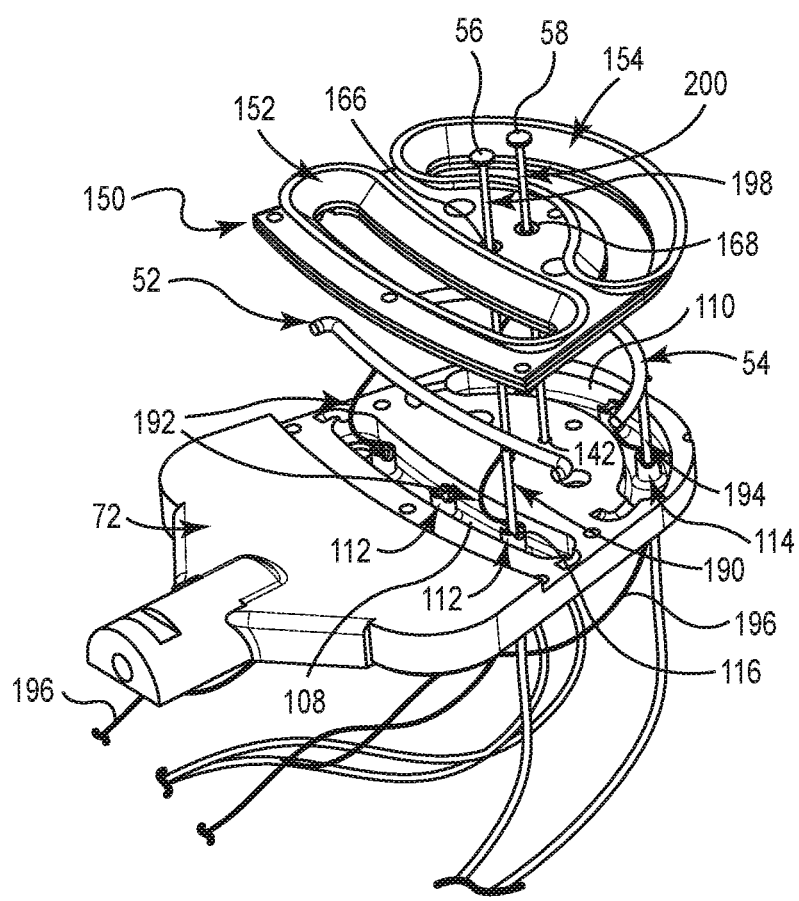
FIG. 7 is a exploded, perspective view illustrating assembly of various components of the head assembly of FIG. 3.

Construction of the head assembly 40 includes mounting of the ablation electrodes 52, 54, the auxiliary electrodes 56, 58, and the tissue contact member 150 to the head 72 as shown in FIG. 7. The first ablation electrode 52 is mounted within the first slot 108 via the fingers 112. In this regard, a primary wire 190 is electrically connected to the first ablation electrode 52, and is threaded through the through hole 116 in one of the fingers 112. One or more secondary wires 192 can also be provided, and electrically connected to sensing elements (e.g., thermocouples) carried by the first ablation electrode 52. Where provided, the secondary wires 192 are threaded through holes 116 of corresponding ones of the fingers 112. The second ablation electrode 54 is similarly mounted within the second slot 110, with a primary wire 194 and optional secondary wires 196 (e.g., with embodiments in which the second ablation electrode 54 carries thermocouples or other sensing-type components) electrically connected to the second ablation electrode 54 and passed through holes 116 in corresponding ones of the fingers 114. The optional first auxiliary electrode 56 is electrically connected to a first sensor wire 198 that in turn is inserted through the first auxiliary opening 166 in the tissue contact member 150 and the first auxiliary hole 140 (hidden in FIG. 7) in the head 72. Similarly, a second sensor wire 200, otherwise electrically connected to the second auxiliary electrode 58, is passed through the second auxiliary opening 168 in the tissue contact member 150 and the second auxiliary hole 142 in the head 72. Finally, the tissue contact member 150 is mounted to the head 72 such that the first skirt 152 surrounds the first ablation electrode 52 and the second skirt 154 surrounds the second ablation electrode 54.

Though not shown in FIG. 7, liquid lines or tubes 204, 206 (FIG. 5) are located along the rear face 124 (FIG. 6B) of the head 72 and inserted into respective ones of the irrigation holes 120a, 120b (best shown in FIG. 6A) so as to be fluidly open to the corresponding slot 108, 110. Similarly, a vacuum line or tube (not shown) is fluidly connected to the bore 130. The head 72 is then assembled to the base 70 (FIG. 5). The various wires 190-200 and tubes 204, 206 are fed through the chamber 88 and along the trough 86 for subsequent insertion through the tubular member 42.

Final construction of the head assembly 40 with the tubular member 42 is shown in FIG. 3. The first and second ablation electrodes 52, 54 are exteriorly exposed relative to a contact face 210 of the head assembly 40. As used in this specification, the "contact face" is in reference to a side or surface of the head assembly 40 intended to be brought into contact with tissue to be ablated. While the skirts 152, 154 project outwardly beyond the corresponding ablation electrodes 52, 54, the suction regions or pods 158, 160 are exteriorly open such that the ablation electrodes 52, 54 are exteriorly exposed and can be brought into ablative contact with tissue otherwise abutting the contact face 210. FIG. 3 further reflects that the optional auxiliary electrodes 56, 58 are exteriorly exposed at the contact face 210, and are located between the ablation electrodes 52, 54. As made clear below, during use of the ablation instrument 22, the ablation electrodes 52, 54 are operable to complete a desired conductive block pattern. By locating the auxiliary sensing electrodes 56, 58 between the ablation electrodes 52, 54, the ablation instrument 22 can further be employed to evaluate a completeness of the so-formed conductive block pattern immediately after the ablation steps are complete and without movement of the contact face 210 relative to the target site.

As described above, the paddle body 50 is sized and shaped for accessing various anatomical locations, such as epicardial tissue at the posterior left atrium, via a subxiphoid surgical approach. The size and shape of the paddle body 50 facilitates this implementation. As such, while the ablation electrodes 52, 54 are generally elongated, the terminal ends thereof do not project beyond the outer perimeter 60 of the paddle body 50. Instead, the ablation electrodes 52, 54 are arranged within a footprint of the paddle body 50, and thus are readily positioned at a desired target site via a subxiphoid surgical approach, for example along epicardial tissue of the posterior left atrium at superior and inferior aspects of the pulmonary vein junction spacing.

Returning to FIG. 5, the tubular member 42 is generally configured to house various lines and wiring extending from the head assembly 40. In general terms, the tubular member 42 has an outer diameter appropriate for subxiphoid placement, and a length sufficient to deliver the head assembly 40 to the posterior left atrium via a subxiphoid incision. In some constructions, the tubular member 42 is a corrugated tube, such as a stainless steel corrugated tube. Thus, the tubular member 42 is at least somewhat malleable, capable of self-maintaining a desired shape. A distal end 212 of the tubular member 42 is configured for attachment to the head assembly 40, for example via one or more internal shoulders 214 (referenced generally) configured to be captured by a corresponding feature of the paddle body neck regions 80, 100. Other mounting configurations are equally acceptable. A proximal end 216 of the tubular member 42 is similarly constructed for mounting to the handle assembly 44 (FIG. 2). Regardless, a lumen 218 is defined through the tubular member 42, serving as a conduit for various components extending from the head assembly 40.

With reference to FIG. 2, the handle assembly 44 can assume various forms, and in some constructions includes a housing 220 (referenced generally), an actuator mechanism 222, and a connector 224. In general terms, the housing 220 is coupled to the tubular member 42, and maintains the actuator mechanism 222. The actuator mechanism 222, in turn, operates to control fluid flow through the liquid tubes 204, 206 and the vacuum line or tube (not shown). Finally, the connector 224 extends from the housing 220 and facilitates connection to the power source 24/controller 26 (FIG. 1), and the vacuum source 28 (FIG. 1), and the liquid source 30 (FIG. 1).

The housing 220 is sized and shaped for convenient handling by a user. In some embodiments, the housing 220 is formed by first and second shell portions 230, 232 that are mateable to one another in a manner capturing the proximal end 216 of the tubular member 42. The actuator mechanism 222 includes a lever or trigger 240 that is pivotably coupled to the housing 220. A catch 242 captures the liquid tubes 204, 206 and the vacuum tube (not shown) relative to an engagement feature 244 of the lever 240. In a normal or first position of the lever 240 relative to the housing 220, the engagement feature 244 applies a pinching force to the liquid tubes 204, 206 and the vacuum tube, thereby preventing fluid flow therethrough. Conversely, in a second, user-actuated position of the lever 240 relative to the housing 220, the engagement feature 244 is spaced from the liquid and vacuum tubes 204, 206 to permit fluid flow therethrough. A biasing member 246 (e.g., spring) biases the lever 240 to the normal position relative to the housing 220. Other fluid flow control mechanisms can alternatively be employed. Further, while in some embodiments the delivery of power to the ablation electrodes 52, 54 is controlled by an actuator (not shown) apart from the handle assembly 44 (e.g., a footswitch), in other constructions the handle assembly 44 can facilitate user control over application of ablative energy.

The connector 224 can be an extruded tubing-type component, providing one or more passageways 250 through which various items can pass. For example, a first passageway 250a serves as a cabling pathway and through which the various wires (not shown) extending from the head assembly 40 as described above are maintained. A second passageway 250b serves as an aspiration or negative pressure pathway, and is fluidly connected to the vacuum line (not shown) described above. Finally, a third passageway 250c serves as a liquid delivery conduit and through which liquid irrigation (e.g., saline) is delivered to the liquid tubes 204, 206.

The handle assembly 44 can optionally incorporate one or more additional features. For example, an indicator device 260 can be maintained by the housing 220, and includes, for example, a light source 262 (e.g., an RGB LED) and a lens 264. As described below, the indicator device 260 is electronically connected to the controller 26 (FIG. 1) and operates to provide a user with a visual indication of various procedural parameters (e.g., the indicator device 260 emits a green colored light when conduction block has been achieved, and a red colored light when conduction block criteria have not been met).

Returning to FIG. 1, the power source 24 can assume various forms, and generally includes an RF energy generator appropriate for supplying sufficient energy to ablate epicardial tissue. For example, the generator provided with the power source 24 can be an ablation energy generator available from Medtronic, Inc., under the trade name Cardioblate® Model 68000 Generator.

In addition to the generator, the power source 24 can include or be operatively connected to the controller 26 that includes a computer or other logic circuitry capable of effectuating one or more of the testing procedures or protocols described below (e.g., hardware or software programs). For example, the controller 26 can be akin to a model 2090/2290 Programmer/Analyzer available from Medtronic, Inc. As used through this specification, then, reference to a "controller" includes a single controller or two or more electronically linked controllers or computing devices.

With cardiac ablation procedures in accordance with some aspects of the present disclosure, radio frequency energy is employed, with the ablation instrument 22 (and the corresponding power source 24) adapted to deliver a maximum of 30 watts of power at 500 kilohertz for two minutes. Other ablation parameters (e.g., energy type, voltage, current, frequency, etc.), can alternatively be employed. The controller 26 can be programmed with one or more algorithms known in the art for monitoring power and/or impedance values at the ablation electrodes 52, 54 throughout an ablation procedure for safety purposes.

One optional testing protocol provided with the controller 26 is a pacing procedure. In general terms, the heart is "paced" by a low frequency signal from an external energy source to control the beating rate of the heart. Typically, a beating rate of 20-30 beats per minute faster than the patient's then-current heart rate is chosen. When the heart rate is controlled by the external energy source, the pacing is considered to have "captured" control of the heart. With this in mind, the controller 26 can be programmed to perform a pacing protocol by causing stimulating or pacing energy to be delivered to the auxiliary electrodes 56, 58, effectively electrically coupling the auxiliary electrodes 56, 58 so that energy passes between the auxiliary electrodes 56, 58. In this regard, the controller 26 can deliver pacing energy from the power source 24. Alternatively, the pacing energy can be generated by an auxiliary energy source (not shown), such as an external temporary pacemaker (e.g., an external temporary pacemaker available from Medtronic, Inc., under Model 5348 or Model 5388).

In some configurations, a pacing threshold is less than 10 mA at 0.5 msec using Medtronic's Model 5388 temporary pacemaker. In the context of use on cardiac tissue, if the heart does not respond to an initial pulsed current, the current may be increased until the heart rate responds to the stimulation. The stimulation or pacing energy can be increased or decreased to attain capture where desired. For example, a pacing amplitude in the range of 0.1-10.0 volts and a current in the range of 0.1-24 milliamp can be provided.

Yet another optional non-ablation procedure available with some embodiments of the controller 26 is a sensing protocol in which electrical activity propagating along cardiac tissue is monitored or sensed. With the auxiliary electrodes 56, 58 placed into contact with desired cardiac tissue, the controller 26 effectively establishes an electrical coupling between the auxiliary electrodes 56, 58, for example by operating the first auxiliary electrode 56 as a positive pole and the second auxiliary electrode 58 as a negative pole (or vice-versa). In contrast to the pacing application, however, the controller 26 does not deliver energy to the auxiliary electrodes 56, 58. Instead, an electrical signal (typically a voltage measurement) progressing across the auxiliary electrodes 56, 58 is monitored. For example, intrinsic electrical activity across contacted tissue (e.g., a depolarizing wave) will progress from the first auxiliary electrode 56 to the second auxiliary electrode 58 (or vice-versa). As the depolarizing wave progresses from the first auxiliary electrode 56 to the second auxiliary electrode 58 (or vice-versa), the controller 26 (or an electronically-linked analyzer) monitors or senses the changing electrical signal(s), and can record or otherwise note various attributes.

The optional vacuum source 28 can assume a variety of forms appropriate for generating desired negative pressure levels. For example, the vacuum source 28 can be a pump. Alternatively, a wall-mounted vacuum source conventionally available in many hospital operating rooms can be utilized.

The optional liquid source 30 can also assume any conventional form. For example, the liquid source 30 can be a flexible bag of liquid saline. Alternatively, a mechanized pump can be included.

Figure 8:
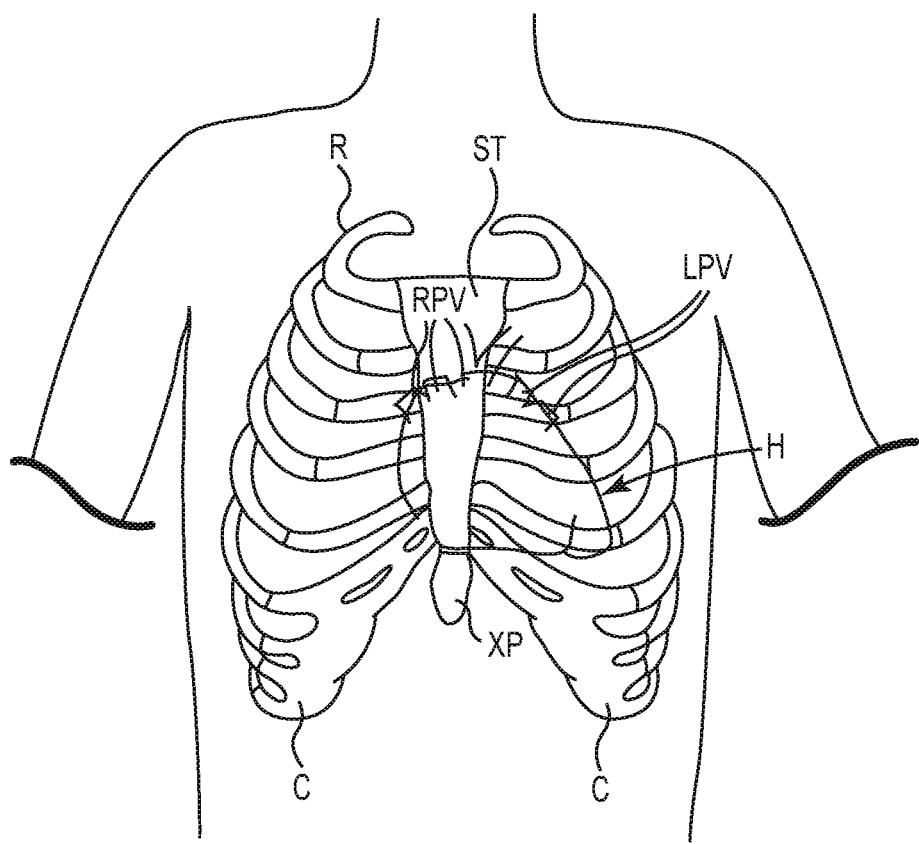
FIG. 8 is a simplified representation of various anatomy of a patient's chest.
Figure 9A:
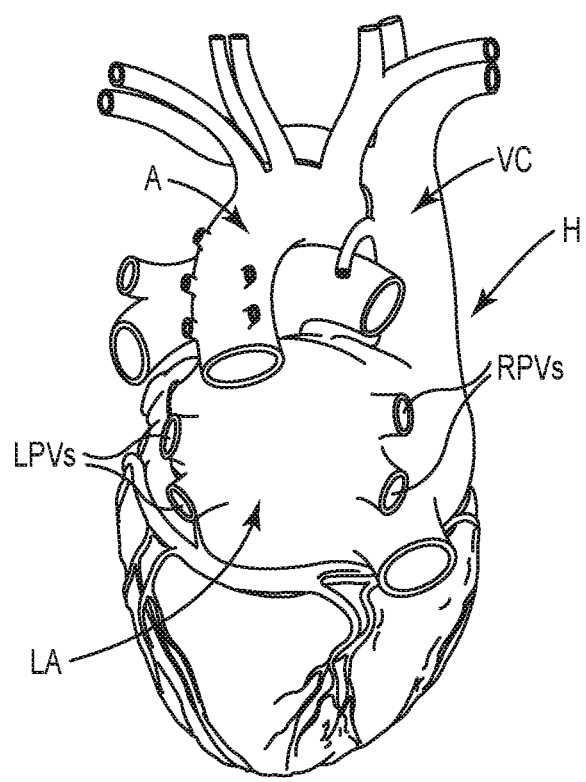
FIG. 9A is a posterior view of a human heart.
Figure 9B:
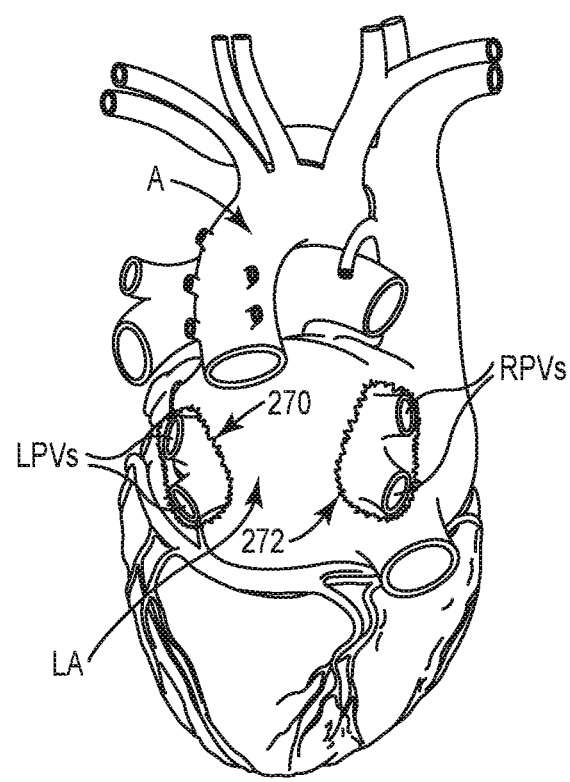
FIG. 9B is a posterior view of the human heart of FIG. 9A and illustrating island lesion patterns formed about junctions between pulmonary veins and left atrium.

The ablation system 20 can be employed to perform various tissue ablation procedures. One such procedure relates to the treatment of cardiac arrhythmia, and in particular atrial fibrillation, by forming lesions on epicardial tissue of the patient. With this in mind, FIG. 8 is a simplified representation of the relevant anatomy of a patient (from an anterior perspective), reflecting a location of the heart H relative to the patient's chest C, including the sternum ST and ribcage R. A xiphoid process XP projects from the ribcage R. The heart H is arranged relative to the chest C such that right pulmonary veins RPVs and left pulmonary veins LPVs are posterior and superior. A posterior view of the heart H is generally reflected in FIG. 9A, and illustrates the right pulmonary veins RPVs and the left pulmonary veins LPVs entering into the top of the left atrium LA. The vena cava VC and aorta A are also shown. With these designations in mind, one cardiac arrhythmia treatment method entails, prior to use of the ablation instrument 22 (FIG. 1), forming a first ablation lesion pattern 270 into the left atrium LA around or encircling the left pulmonary veins LPVs (i.e., the junction of the left pulmonary veins LPVs with the left atrium LA) and a second ablation lesion pattern 272 around the right pulmonary veins RPVs as reflected in FIG. 9B. The first and second ablation patterns 270, 272 are commonly referred to as "island patterns," and can be formed in various manners, for example via a clamp-type surgical ablation device available from Medtronic, Inc, under the trade name Cardioblate® Gemini™. Regardless, the ablation instrument 22 is then employed to form lesion patterns along epicardial tissue of the posterior left atrium LA that interconnects the islands 270, 272.

Figure 10A:
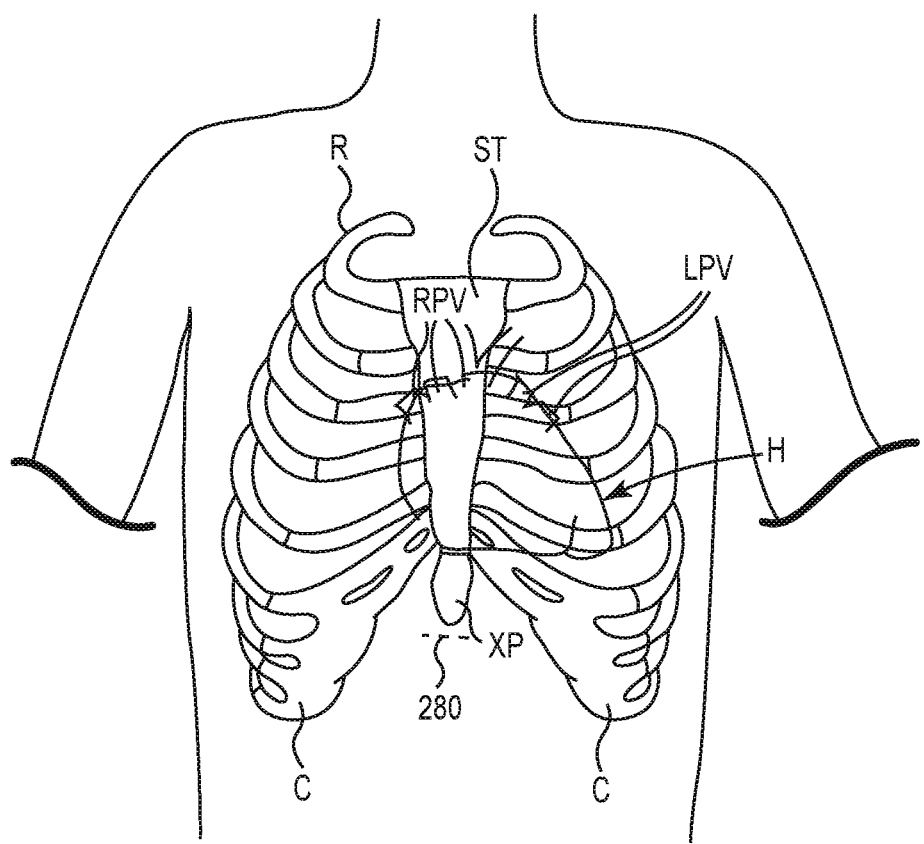
FIGS. 10A-10E illustrate methods in accordance with the present disclosure including the ablation system of FIG. 1 employed to complete a portion of a conductive block ablation pattern on the posterior left atrium via a subxiphoid surgical approach.
Figure 10B:
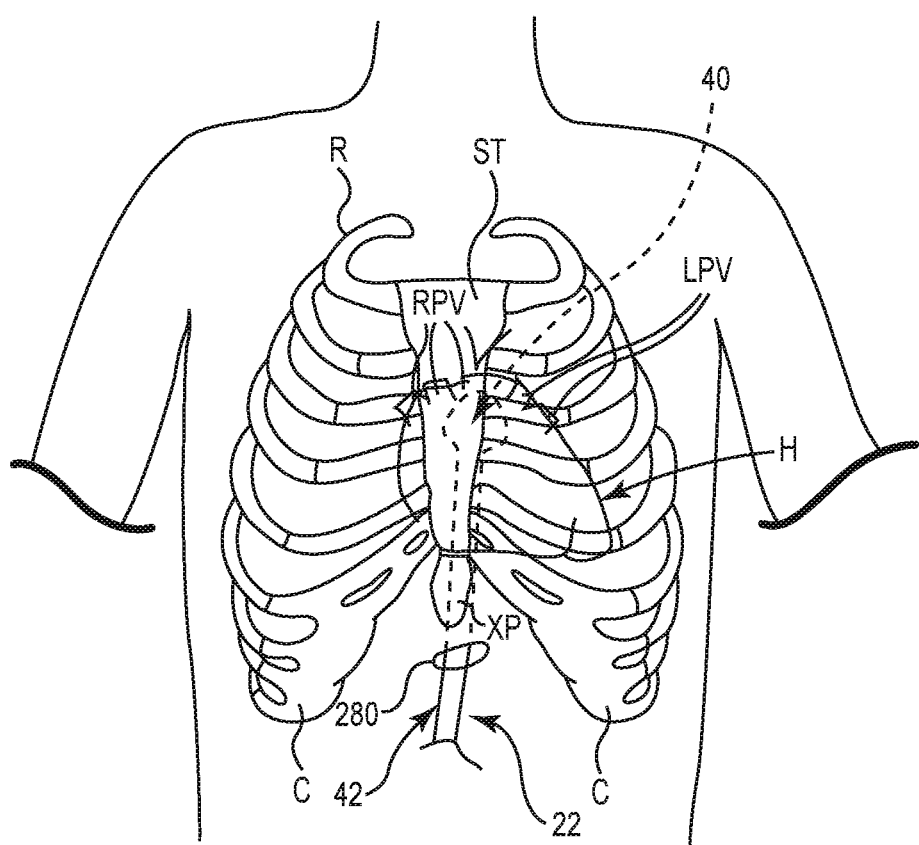
Figure 10C:
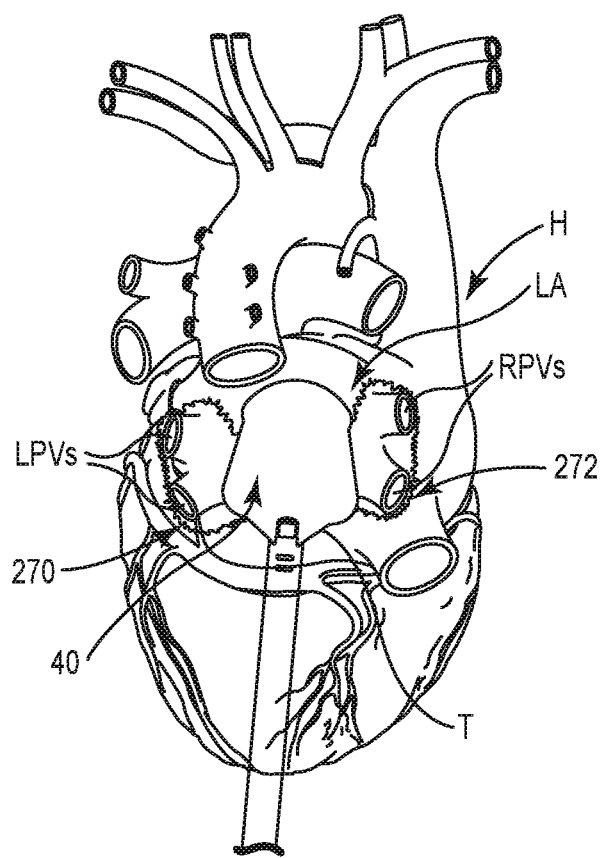

In particular, and with reference to FIG. 10A, an incision 280 is formed immediately beneath the xiphoid process XP, thereby establishing a subxiphoid access or surgical approach to the heart H. As a point of reference, the subxiphoid incision 280 may have been previously formed, for example in connection with the formation of the island ablation patterns described above. The ablation instrument 22 is then manipulated to position the head assembly 40 (FIG. 2) against the posterior left atrium LA as shown in FIG. 10B. In particular, the head assembly 40 is inserted through the subxiphoid incision 280, and directed posteriorly and superiorly about a posterior aspect of the heart H. The malleable nature of the tubular member 42 in some embodiments affords the surgeon the ability to accommodate various anatomical obstacles presented by the particular patient. Regardless, and as shown in FIG. 10C, the head assembly 40 is positioned such that the contact face 210 (hidden in FIG. 10C, but shown, for example, in FIG. 3) abuts epicardial tissue of the posterior left atrium LA.

Figure 10D:
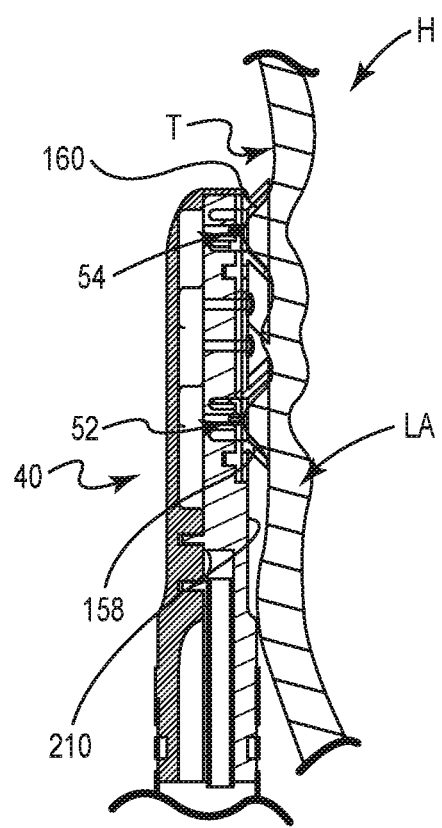
Figure 10E:
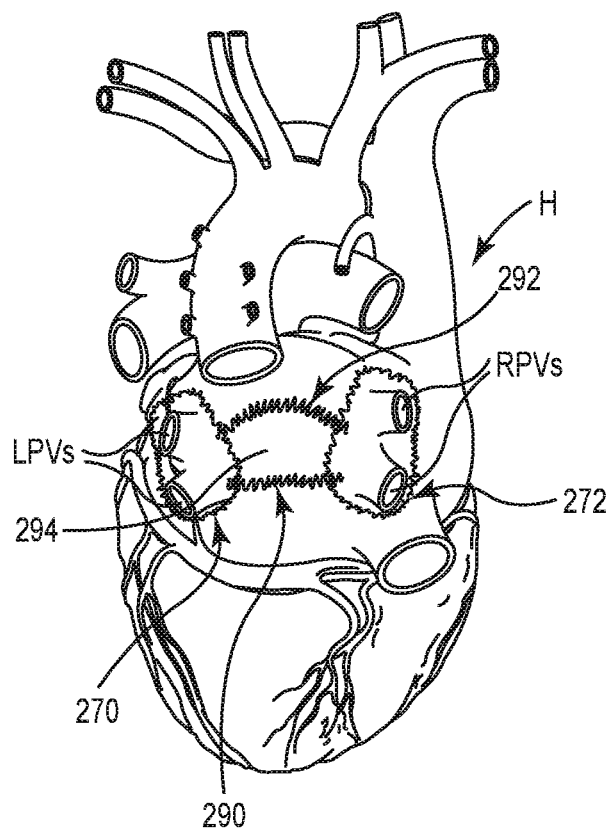

The vacuum source 28 (FIG. 1) is then activated. With the additional reference to FIG. 10D, negative pressure is thereby established at the first and second suction regions 158, 160, drawing epicardial tissue T of the posterior left atrium LA into intimate contact with the corresponding ablation electrodes 52, 54. Though not fully illustrated in FIG. 10D, in some embodiments the skirts 152, 154 will elastically collapse or deflect in the presence of negative pressure in the suction regions 158, 160, effectively establishing a consistent holding force of the epicardial tissue T along, and in intimate contact with, the corresponding ablation electrodes 52, 54. The ablation electrodes 52, 54 are evenly pressed against the targeted tissue T. The power source 24 (FIG. 1) is then activated in a manner to deliver ablative energy to the first ablation electrode 52 for a time sufficient to ablate the contacted tissue. The second ablation electrode 54 is sequentially energized by the power source 24 for a time sufficient to ablate contacted tissue. By providing the intimate, consistent or uniform contact between the targeted tissue T and the ablation electrodes 52, 54 as described above, predictable ablations (in terms of, for example, transmurality, conduction block, etc.) can be achieved. The ablation electrodes 52, 54 can be sequentially operated in any order, or can be simultaneously energized. For safety purposes, the temperature of the ablation electrodes 52, 54 can be closely monitored by the controller 26 (FIG. 1), for example by electrical connection to the optional thermocouples carried by the ablation electrode ends 176, 178, 180, 182 (FIG. 5). The liquid source 30 (FIG. 1) can be simultaneously activated to irrigate and cool the ablation electrodes 52, 54. For example, the liquid source 30 and the vacuum source 28 can be fluidly connected to the head assembly 40 in tandem. The irrigation or cooling liquid (e.g., cooled or room temperature saline) enters the suction regions 158, 160 and cools the corresponding ablation electrode 52, 54; the now-heated liquid is subsequently evacuated from the suction regions 158, 160 via the suction apertures described above. Notably, when the head assembly 40 is positioned at the target site (e.g., posterior left atrium) and suction applied, the clinician can optionally perform a "hands-free" ablation, allowing the clinician to complete other tasks while the ablation is taking place. Regardless, operation of the instrument 22 results in first and second connective ablation lesions 290, 292 as shown in FIG. 10E.

Figure 4:
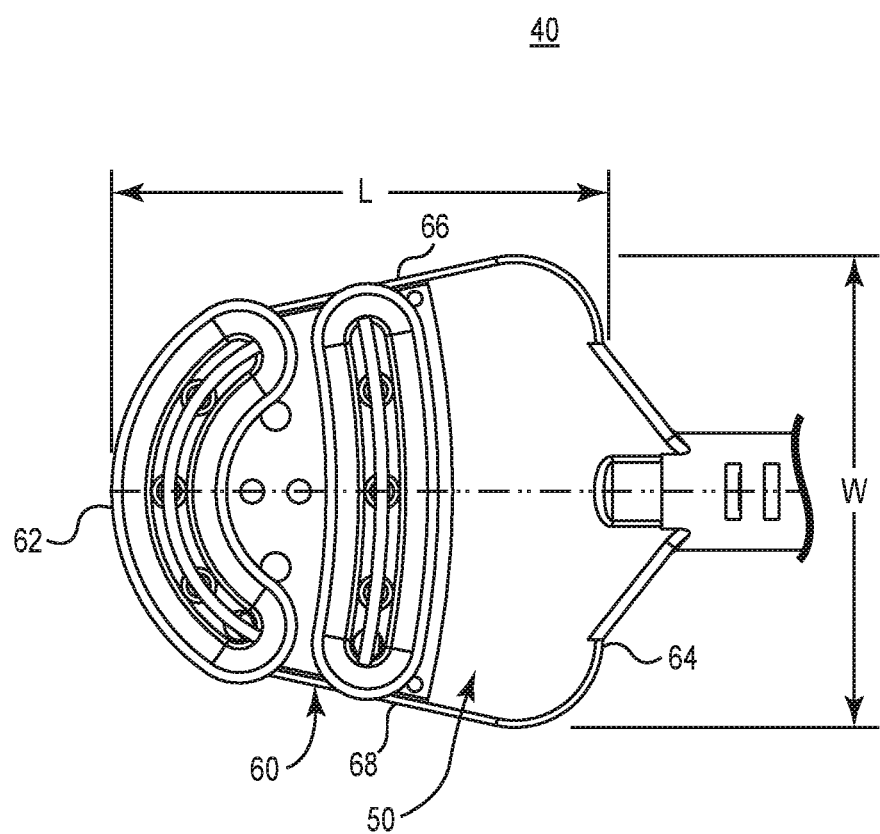
FIG. 4 is a top plan view of the head assembly of FIG. 3.

The connective lesions 290, 292 interconnect the island patterns 270, 272, thereby establishing a conductive block or "box" area 294 between junctions of the left pulmonary veins LPVs and the right pulmonary veins RPVs with the left atrium LA. As reflected in FIG. 10E, the necessary length of the first connective lesion 290 (i.e., sufficient to extend from and between the first island 270 and the second island 272 at an inferior aspect thereof) corresponds with a length of the first ablation electrode 52 (FIG. 4), whereas a length of the second connective lesion 292 (i.e., sufficient to interconnect the first and second islands 270, 272 along a superior aspect thereof) corresponds with a length of the second ablation electrode 54 (FIG. 4). Thus, the desired connective lesions 290, 292 are formed by the ablation instrument 22 without requiring movement of the head assembly 40 once the delivery of ablative energy has been initiated. In other embodiments, however, the ablation instrument 22 can be operated to form a first segment of the first and second connective lesions 290, 292, and then moved transversely relative to the heart H to form corresponding second segments of the connective lesions 290, 292.

In some embodiments, the system 20 (FIG. 1) can further be operated to confirm successful completion of the connective lesions 290, 292 (i.e., that the conductive block 294 is electrically isolated). For example, the controller 26 (FIG. 1) can be operated, or caused to be operated, to perform pacing and/or sensing procedures immediately following delivery of ablative energy to the ablation electrodes 52, 54. To this end, by desirably positioning the auxiliary electrodes 56, 58 spatially between the ablation electrodes 52, 54, the auxiliary electrodes 56, 58 will inherently be located "within" the confines of the conductive block 294. Thus, the auxiliary electrodes 56, 58 are properly located for desired conduction block testing upon initial placement (i.e., immediately prior to ablating with the ablation electrodes 52, 54) of the contact face 210 (FIG. 3) against the posterior left atrium LA; as such, testing can be performed immediately following completion of the connective lesions 290, 292, and the surgeon is not required to re-position the head assembly 40. With the head assembly 40 remaining in the same location relative to the epicardial tissue T (as in FIGS. 10C and 10D), the controller 26 operates the auxiliary electrodes 56, 58 in a bipolar mode to perform pacing test(s) (i.e., delivering the pacing energy as described above). For example, as part of an exit block test, pacing energy is applied "within" the conductive block 294 and an evaluation is made as to whether or not the rest of the heart is "captured" in response. With some techniques, prior to ablating the connective lesions 290, 292, a pacing energy sufficient to capture the heart is applied and the corresponding power settings are recorded. The exit block test can then consist of a determination as to whether the heart is "captured" at the same power settings. When the heart cannot be captured using the same pre-ablation power settings, an initial determination can be made that the conductive block 294 was successful in isolating the target site. In other embodiments, if capture is not achieved at the pre-ablation power settings, the power output can then be increased (e.g., doubled) and a determination made as to whether the heart is "captured" at this increased power output. If capture is not achieved at this double power heart pacing, the conductive block 294 can be considered to be isolated and exit blocking from this area proven. Conversely, where the heart is captured during the post-ablation exit block test, an indication is given that the ablation lesion patterns 270, 272, 290, 292 were not successful in isolating the target site 294, and the surgeon can then repeat the ablation procedure and/or form additional lesion pattern(s) in other areas.

An entrance block test can also or alternatively be used to evaluate the effectiveness of the ablation patterns 270, 272, 290, 292. In particular, the controller 26 (FIG. 1) operates the auxiliary electrodes 56, 58 to sense electrical activity within the conductive block 294. The monitored output may be recorded and saved as a visual "ECG" type output and the collection of monitored information visually compared to each other. Alternatively or in addition, an algorithm can be programmed to the controller 26 and used to compare the captured output; if the difference between the electrical activity prior to the ablation (e.g., atrial P-wave) is reduced a significant amount (e.g., 80% reduction), it can be assumed that the target site 294 has been successfully blocked. Conversely, if an insignificant difference is determined, additional lesion patterns can be formed. Additionally or alternatively, with the auxiliary electrodes 56, 58 being operated by the controller 26 in a sensing mode, a pacing energy is applied to the heart outside of the conductive block region 294. If the auxiliary electrodes 56, 58 (otherwise in contact with epicardial tissue inside of the conductive block 294) do not sense the so-applied pacing energy, it can be positively concluded that entrance block has been achieved.

In some embodiments, the controller 26 (FIG. 1) can be programmed with set confirmation parameters and operate to automatically alert the surgeon as to the results of the conduction block testing. For example, following ablation with the ablation electrodes 52, 54 (FIG. 3) as described above, the controller 26 can automatically perform one or more of the pacing/sensing tests. If the results of one or more of these tests (e.g., the pre- and post-ablation atrial P-wave comparison test described above) are viewed by the controller 26 as being indicative of unsuccessful conduction block, the indicator device 260 (FIG. 2) is operated to provide a warning to the surgeon (e.g., a red light). Conversely, when the controller 26 deems the test result(s) as implicating successful conduction block, the indicator device 260 is operated by the controller 26 to provide a confirmation to the surgeon (e.g., a green light). Other indicating techniques can be employed (e.g., graphical display, audible noise, etc.). Alternatively, the indicator device 260 can be omitted.

While the head assembly 40 (FIG. 3) has been described as having the first and second ablation electrodes 52, 54 (FIG. 3) with the shapes described above, other configurations are also acceptable. For example, FIG. 11A is a simplified view of another head assembly 300 in accordance with principles of the present disclosure and useful with the ablation instrument 22 (FIG. 1). The head assembly 300 generally includes a paddle body 302, ablation electrodes 304a-304d, and auxiliary electrodes 306a, 306b. The paddle body 302 is sized and shaped for a subxiphoid surgical approach to the posterior left atrium, and can have the wedge-like shape as shown. The electrodes 304a-306b are maintained by, and are exteriorly exposed relative to a contact face 308 of, the paddle body 302 in a spatially fixed manner. The ablation electrodes 304a-304d are akin to the ablation electrodes 52, 54 described above and are segmented about (and in close proximity to) a perimeter of the paddle body 302a-302d. The auxiliary electrodes 306a, 306b are akin to the auxiliary electrodes 56, 58 (FIG. 3) described above, and are located within a perimeter of the ablation electrodes 304a-304d for performing pacing/sensing operations as described above. In other embodiments, the auxiliary electrodes 306a, 306b can be omitted. During use, the contact face 308 is directed against targeted tissue and the ablation electrodes 304a-304d sequentially energized to ablate a portion of a conductive block region, for example along epicardial tissue of the posterior left atrium between the left and right pulmonary vein junctions to interconnect superior and inferior aspects of separately-formed island lesions. Other features described above (e.g., suction regions, liquid supply/cooling, etc.) can be optionally incorporated into the head assembly 300.

Another embodiment of a head assembly 310 in accordance with principles of the present disclosure and useful with the ablation instrument 22 (FIG. 1) is shown, in simplified form, in FIG. 11B. The head assembly 310 includes a paddle body 312, primary ablation electrodes 314a-314d, a secondary ablation electrode 316, and auxiliary electrodes 318a, 318b. The paddle body 312 is sized and shaped for delivery to the posterior left atrium via a subxiphoid surgical approach, and can have the wedge-like shape as shown. The electrodes 314a-318b are maintained by, and are exteriorly exposed relative to a contact face 320 of, the paddle body 312 in a spatially fixed manner. The primary ablation electrodes 314a-314d are segmented about (and in close proximity to) a perimeter of the paddle body 312, and are akin to the ablation electrodes previously described. The secondary ablation electrode 316 is arranged generally parallel with, but spaced from, the first primary ablation electrode 314a (i.e., a linear distance between the secondary ablation electrode 316 and the fourth primary ablation electrode 314d is less than a linear distance between the first primary ablation electrode 314a and the fourth primary ablation electrode 314d). The auxiliary electrodes 318a, 318b are akin to the auxiliary electrodes described above, and are positioned within a perimeter defined by the second-fourth primary ablation electrodes 314b-314d and the secondary ablation electrode 316 for performing pacing/sensing protocols as described above. In other embodiments, the auxiliary electrodes 318a, 318b can be omitted. During use, the contact face 320 is directed against targeted epicardial tissue and the primary ablation electrodes 314a-314d sequentially energized to create a portion of a conductive block lesion pattern, for example along epicardial tissue of the posterior left atrium between the left and right pulmonary vein junctions to interconnect superior and inferior aspects of separately-formed island lesions. In instances where the anatomy of the patient's heart is such that the first primary ablation electrode 314a is too close to certain anatomical structures (e.g., the AV groove), the secondary ablation electrode 316 can be energized instead of the first primary ablation electrode 314a. Other features described above (e.g., suction regions, liquid supply/cooling, etc.), can optionally be incorporated into the head assembly 310.

Another embodiment head assembly 330 in accordance with principles of the present disclosure and useful with the ablation instrument 22 (FIG. 1) is shown, in simplified form, in FIG. 11C. The head assembly 330 includes a paddle body 332, ablation electrodes 334a-334d, and auxiliary electrodes 336a, 336b. The paddle body 332 is akin to the configurations described above, and can have a generally wedge-like shape for interfacing with the posterior left atrium via a subxiphoid surgical approach. With the construction of FIG. 11C, however, opposing sides 338a, 338b of the paddle body 332 flare radially outwardly (as compared to the shape of FIGS. 11A and 11B). Regardless, the electrodes 334a-336b are maintained by, and exteriorly exposed relative to a contact face 340 of, the paddle body 332 in a spatially fixed manner. The ablation electrodes 334a-334d are akin to those above and are segmented about (and in close proximity to) a perimeter of the paddle body 332, including the flared edges 338a, 338b. With this construction, when the contact face 340 is positioned against the posterior left atrium between the left and right pulmonary vein junctions, the second and third ablation electrodes 334b, 334c are more likely positioned to intersect with the pulmonary vein island ablation patterns (e.g., the island lesions 270, 272 of FIG. 9B). The auxiliary electrodes 336a, 336b are akin to the auxiliary electrodes described above, and can be operated to perform various pacing and/or sensing protocols. In other embodiments, the auxiliary electrodes 336a, 336b can be omitted. Other features described above (e.g., suction regions, liquid supply/cooling, etc.) can optionally be incorporated into the head assembly 330.

Yet another embodiment of a head assembly 350 in accordance with principles of the present disclosure and useful with the ablation instrument 22 (FIG. 1) is shown, in simplified form, in FIG. 11D. The head assembly 350 includes a paddle body 352, ablation electrodes 354a-354d, and auxiliary electrodes 356a, 356b. The paddle body 352 is sized and shaped for delivery to the posterior left atrium via a subxiphoid surgical approach, and can have the generally oval-like shape reflected in FIG. 11D. The electrodes 354a-356b are maintained by, and exteriorly exposed relative to a contact face 358 of, the paddle body 352 in a spatially fixed manner. The ablation electrodes 354a-354d are segmented about (and in close proximity to) a perimeter of the paddle body 352, and are otherwise akin to the ablation electrodes described above. The auxiliary electrodes 356a-356b are optional, and are akin to the auxiliary electrodes described above for performing one or more pacing/sensing protocols. During use, the contact face 358 is directed against targeted epicardial tissue and the ablation electrodes 354a-354d sequentially energized to ablate a portion of a conductive blank region, for example, along epicardial tissue of the posterior left atrium between the pulmonary vein junctions to interconnect superior and inferior aspects of separately-formed island lesions. Other features described above (e.g., suction regions, liquid supply/cooling, etc.) can optionally be incorporated into the head assembly 350.

Yet another embodiment head assembly 360 in accordance with principles of the present disclosure and useful with the ablation instrument 22 (FIG. 1) is shown, in simplified form, in FIG. 11E. The head assembly 360 includes a paddle body 362, ablation electrodes 364a-364c, a first pair of auxiliary electrodes 366a, 366b and a second pair of auxiliary electrodes 368a, 368b. The paddle body 362 is sized and shaped for delivery to the posterior left atrium via a subxiphoid surgical approach, and can have the wedge-like shape as shown. The electrodes 364a-368b are maintained by, and are exteriorly exposed relative to a contact face 370 of, the paddle body 362 in a spatially fixed manner. The ablation electrodes 364a-364c are mounted to the paddle body 362 in a segmented fashion, generally defining the Z-like pattern shown. For example, the first and third ablation electrodes 364a, 364c can be generally parallel to one another, with the second ablation electrode 364b extending from the first ablation electrode 364a at a first side of the paddle body 362 to the third ablation electrode 364c at an opposite side of the paddle body 362. The auxiliary electrode pairs 366a, 366b, 368a, 368b are located at opposite sides of the second ablation electrode 364b. With this construction, the contact face 370 can be directed into contact with epicardial tissue of the posterior left atrium via a subxiphoid surgical approach, with the first and third ablation electrodes 364a, 364c being sequentially energized to form lesions that interconnect superior and inferior aspects of separately-formed formed island ablation patterns as described above. The second ablation electrode 364b also defines an ablation lesion, with the auxiliary electrode pairs 366a, 366b and 368a, 368b being operated to evaluate desired conduction block. Other features described above (e.g., suction regions, liquid supply/cooling, etc.) can optionally be incorporated into the head assembly 360.

Another alternative head assembly 380 in accordance with principles of the present disclosure and useful with the ablation instrument 22 (FIG. 1) is shown, in simplified form, in FIG. 11F. The head assembly 380 includes a paddle body 382, ablation electrodes 384a-384c, a first pair of auxiliary electrodes 386a, 386b and a second pair of auxiliary electrodes 388a, 388b. The head assembly 380 is highly akin to the head assembly 360 (FIG. 11E) described above, with the paddle body 382 being sized and shaped to access the posterior left atrium via a subxiphoid surgical approach. With the construction of FIG. 11F, however, the paddle body 382 has a clover-like shape with flared sides. The electrodes 384a-388b are maintained by, and exteriorly exposed relative to a contact face 390 of, the paddle body 382 in a spatially fixed manner. The first and third ablation electrodes 384a, 384c extend along (and in close proximity to) portions of a perimeter of the paddle body 382 as shown, with the second ablation electrode 384b extending in the angular fashion shown (segmented from the first and third ablation electrodes 384a, 384c). The auxiliary electrode pairs 386a, 386b and 388a, 388b are arranged at opposite sides of the second ablation electrode 384b, and are operable to perform various pacing and sensing protocols. During use, the contact face 390 is directed against target epicardial tissue and the ablation electrodes 384a-384c sequentially energized to ablate a portion of a conductive block pattern, for example along epicardial tissue of the posterior left atrium between the pulmonary vein junctions to interconnect superior and inferior aspects of separately-formed island ablation regions. Other features described above (e.g., suction regions, liquid supply/cooling, etc.) can optionally be incorporated into the head assembly 380.

Another embodiment head assembly 400 in accordance with principles of the present disclosure and useful with the ablation instrument 22 (FIG. 1) is shown, in simplified form, in FIG. 11G. The head assembly 400 includes a paddle body 402, ablation electrodes 404a-404f, and auxiliary electrodes 406a, 406b. The paddle body 402 is sized and shaped for delivery to the posterior left atrium via a subxiphoid approach, and can have the clover-like shape shown. The electrodes 404a-406b maintained by, and are exteriorly exposed relative to a contact face 410 of, the paddle body 402 in a spatially fixed manner. The ablation electrodes 404a-404f are mounted in a segmented fashion about (and in close proximity to) a perimeter of the paddle body 406. Finally, the auxiliary electrodes 406a, 406b are akin to the auxiliary electrodes described above, and are disposed within an area defined by a pattern of the ablation electrodes 404a-404f. Alternatively, the auxiliary electrodes 406a, 406b can be omitted. With the clover-like shape of the paddle body 402, upon placement of the contact face 410 against epicardial tissue of the posterior left atrium between the pulmonary vein junctions, the second and seventh ablation electrodes 404b, 404f are better positioned to more likely intersect with island lesions as previously described. Other features described above (e.g., suction regions, liquid supply/cooling, etc.) can optionally be incorporated into the head assembly 400.

Yet another embodiment head assembly 420 in accordance with principles of the present disclosure and useful with the ablation instrument 22 (FIG. 1) is shown, in simplified form, in FIG. 11H. The head assembly 420 includes a paddle body 422, primary ablation electrodes 424a-424d, secondary ablation electrodes 426a-426d, and auxiliary electrode pairs 428a-428e. The paddle body 422 is sized and shaped for delivery to the posterior left atrium via a subxiphoid surgical approach, and can have the wedge-like shape shown. The electrodes 424a-428e are maintained by, and are exteriorly exposed relative to a contact face 430 of, the paddle body 422 in a spatially fixed manner. The primary ablation electrodes 424a-424d are mounted in a segmented fashion about (and in close proximity to) a perimeter of the paddle body 422. The secondary ablation electrodes 426a-426d extend generally parallel with the first primary ablation electrode 424a in a spaced apart fashion. Respective ones of the auxiliary electrode pairs 428a-428e are arranged as shown. During use, the contact face 430 is directed against targeted epicardial tissue and some or all of the ablation electrodes 424a-424d and 426a-426d are sequentially energized to ablate corresponding lesion patterns, for example at the posterior left atrium to interconnect superior and inferior aspects of separately-formed pulmonary vein island lesions. Various ones of the auxiliary electrode pairs 428a-428e can be selectively operated to perform various pacing and sensing protocols to evaluate conduction blockage of the resultant lesion pattern. Alternatively, one or more of the auxiliary electrode pairs 428a-428e can be omitted. Other features described above (e.g., suction regions, liquid supply/cooling, etc.) can optionally be incorporated into the head assembly 420.

Another head assembly 440 in accordance with principles of the present disclosure and useful with the ablation instrument 22 (FIG. 1) is shown, in simplified form, in FIG. 11I. The head assembly 440 includes a paddle body 442, ablation electrodes 444a-444d, and an auxiliary electrode pair 446a-446b. The paddle body 442 is sized and shaped for delivery to the posterior left atrium via a subxiphoid surgical approach, and can have the wedge-like shown. In contrast to other embodiments, opposing sides 448a, 448b of the paddle body 442 have a concave shape. With this construction, the opposing sides 448a, 448b may more readily fit between the right and left pulmonary vein junctions, for example with the left atrium. Regardless, the electrodes 444a-446b are maintained by, and are exteriorly exposed relative to a contact face 450 of, the paddle body 442 in a spatially fixed manner. The ablation electrodes 444a-444d are akin to previous embodiments, and are mounted in a segmented fashion about (and in close proximity to) a perimeter of the paddle body 442. The auxiliary electrodes 446a-446d are also akin to other embodiments, and are generally disposed within a pattern defined by the ablation electrodes 444a-444d. The head assembly 440 can be operated in a manner akin to previous descriptions, with the contact face 450 being directed against targeted epicardial tissue, for example along the posterior left atrium between the pulmonary vein junctions and the ablation electrodes 444a-444d sequentially energized to ablate a portion of a conductive block pattern, for example interconnecting superior and inferior aspects of separately-formed island ablation regions. Other features described above (e.g., suction regions, liquid supply/cooling, etc.) can optionally be incorporated into the head assembly 440.

Yet another embodiment head assembly 460 in accordance with principles of the present disclosure and useful with the ablation instrument 22 (FIG. 1) is shown, in simplified form, in FIG. 11J. The head assembly 460 includes a paddle body 462, ablation electrodes 464a, 464b and auxiliary electrodes 466a, 466b. The paddle body 462 is sized and shaped for delivery to the posterior left atrium via a subxiphoid surgical approach. With the construction of FIG. 11J, a trailing region 468 of the paddle body 462 forms or defines transverse protrusions 470a, 470b. The protrusions 470a, 470b are generally configured to contact or engage one of the left pulmonary veins and one of the right pulmonary veins, respectively, when the head assembly 460 is otherwise positioned along the posterior left atrium. Thus, the protrusions 470a, 470b serve to better ensure desired arrangement of the head assembly 460 along the posterior left atrium. The electrodes 464a-466b are maintained by, and exteriorly exposed relative to a contact face 472 of, the paddle body 462 in a spatially fixed manner. The ablation electrodes 464a, 464b are akin to previous embodiments, and are arranged in a spaced apart fashion. The auxiliary electrode 466a, 466b are akin to previous embodiments, and are mounted to the paddle body 462 between the ablation electrodes 464a, 464b. During use, the contact face 472 is directed into contact with epicardial tissue of the posterior left atrium, with the protrusions 470a, 470b engaging respective ones of the left and right pulmonary veins. The ablation electrodes 464a, 464b are sequentially energized to ablate a portion of a conductive block pattern, for example interconnecting superior and inferior aspects of separately-formed island ablation regions as described above. Where provided, the auxiliary electrodes 486a, 486b are employed to perform various pacing/sensing protocols. Other features described above (e.g., suction regions, liquid supply/cooling, etc.) can optionally be incorporated into the head assembly 460.

Another embodiment head assembly 480 in accordance with principles of the present disclosure and useful with the ablation instrument 22 (FIG. 1) is shown, in simplified form, in FIG. 11K. The head assembly 480 includes a paddle body 482, ablation electrodes 484a, 484b, and auxiliary electrodes 486a, 486b. The paddle body 482 is sized and shaped for delivery to the posterior left atrium via a subxiphoid surgical approach, and can have the wedge-like shape shown. The electrodes 484a-486b are maintained by, and are exteriorly exposed relative to a contact face 488 of, the paddle body 482 in a spatially fixed manner. The ablation electrodes 484a, 484b extend in a generally parallel fashion at opposite ends of the paddle body 482, and the auxiliary electrodes 486a, 486b are located between the ablation electrodes 484a, 484b. The head assembly 480 is operable in manners similar to those described above, with the contact face 488 being directed against epicardial tissue of the posterior left atrium between the pulmonary vein junctions. The ablation electrodes 484a, 484b are sequentially energized to ablate a portion of a conductive block pattern, for example interconnecting superior and inferior aspects of separately-formed island ablation regions. The auxiliary electrodes 486a, 486b can be used for various pacing/sensing protocols, but can be omitted. Other features described above (e.g., suction regions, liquid supply/cooling, etc.) can optionally be incorporated into the head assembly 480.

Another embodiment head assembly 490 in accordance with principles of the present disclosure and useful with the ablation device 22 (FIG. 1) is shown, in simplified form, in FIG. 11L. The head assembly 490 includes a paddle body 492, ablation electrodes 494a, 494b, and auxiliary electrodes 496a, 496b. The paddle body 492 is sized and shaped for delivery to the posterior left atrium via a subxiphoid surgical approach, and can have the oval-like shape shown. The electrodes 494a-496b are maintained by, and are exteriorly exposed relative to a contact face 498 of, the paddle body 492 in a spatially fixed manner. The ablation electrodes 494a, 494b extend in a generally parallel fashion at opposite ends of the paddle body 492. The auxiliary electrodes 496a, 496b are mounted to the paddle body 492 between the ablation electrodes 494a, 494b. The head assembly 490 is operable to perform various ablation procedures as described above, including the contact face 498 being directed against epicardial tissue of the posterior left atrium between the pulmonary vein junctions. The ablation electrodes 496a, 496b are sequentially energized to ablate a portion of a conductive block pattern, for example interconnecting superior and inferior aspects of separately-formed island ablation regions. The auxiliary electrodes 496a, 496b can be used for various pacing/sensing protocols, but can be omitted. Other features described above (e.g., suction regions, liquid supply/cooling, etc.) can optionally be incorporated into the head assembly 490.

Another embodiment head assembly 500 in accordance with principles of the present disclosure and useful with the ablation device 22 (FIG. 1) is shown, in simplified form, in FIG. 11M. The head assembly 500 includes a paddle body 502, ablation electrodes 504a, 504b, and auxiliary electrodes 506a, 506b. The paddle body 502 is sized and shaped for delivery to the posterior left atrium via a subxiphoid surgical approach, and can have the generally circular shape shown. The electrodes 504a-506b are maintained by, and are exteriorly exposed relative to a contact face 508 of, the paddle body 502 in a spatially fixed manner. The ablation electrodes 504a, 504b are arranged in a segmented fashion about (and in close proximity to) a perimeter of the paddle body 502. The auxiliary electrodes 506a, 506b are located between or circumscribed by the ablation electrodes 504a, 504b. The head assembly 500 is operable in manners similar to those described above, with the contact face 508 being directed against epicardial tissue of the posterior left atrium between the pulmonary vein junctions. The ablation electrodes 504a, 504b are sequentially energized to ablate a corresponding lesion pattern, for example a lesion pattern interconnecting separately-formed pulmonary vein island lesions. The auxiliary electrodes 506a, 506b can be operated to perform various pacing and/or sensing procedures, or can be omitted. Other features described above (e.g., suction regions, liquid supply/cooling, etc.) can optionally be incorporated into the head assembly 500.

Another embodiment head assembly 510 in accordance with principles of the present disclosure and useful with the ablation device 22 (FIG. 1) is shown, in simplified form, in FIG. 11N. The head assembly 510 includes a paddle body 512, ablation electrodes 514a-514c, and auxiliary electrodes 516a, 516b. The paddle body 512 is sized and shaped for delivery to the posterior left atrium via a subxiphoid surgical approach, and can have the wedge-like shape shown. The electrodes 514a-516b are maintained by, and are exteriorly exposed relative to a contact face 518 of, the paddle body 512 in a spatially fixed manner. The ablation electrodes 514a-514c are arranged in a segmented fashion, defining a C-like pattern as shown. The auxiliary electrodes 516a, 516b are located along the paddle body 512 essentially within the C-like pattern. The head assembly 510 can be employed to perform various ablation and other procedures in ways consistent with previous descriptions, including the contact face 518 being directed against epicardial tissue of the posterior left atrium between the pulmonary vein junctions. The ablation electrodes 514a-514c are sequentially energized to ablate a portion of a conductive block pattern, for example interconnecting superior and inferior aspects of separately-formed island lesions. Other features described above (e.g., suction regions, liquid supply/cooling, etc.) can optionally be incorporated into the head assembly 510.

Another embodiment head assembly 520 in accordance with principles of the present disclosure and useful with the ablation device 22 (FIG. 1) is shown, in simplified form, in FIG. 11O. The head assembly 520 includes a paddle body 522, primary ablation electrodes 524a-524c, secondary ablation electrodes 526a-526c, a first auxiliary electrode pair 528a, 528b, and a second auxiliary electrode pair 530a, 530b. The paddle body 522 is sized and shaped for delivery to the posterior left atrium via a subxiphoid surgical approach, and can have the wide, wedge-like shape shown. In particular, the paddle body 522 defines opposing sides 532a, 532b, with the first side 532a being longer than the second side 532b. The electrodes 524a-530b are maintained by, and are exteriorly exposed relative to a contact face 534 of, the paddle body 522 in a spatially fixed manner. The primary ablation electrodes 524a-524c are arranged in the Z-like pattern shown. The secondary ablation electrodes 526a-526c are also mounted to the paddle body 522 in a segmented fashion, but extend along the first side 532a. With this arrangement, upon deployment of the head assembly 520 along the posterior left atrium, the secondary ablation electrodes 526a-526c can be energized to create a lesion pattern between the superior vena cava and the inferior vena cava. Stated otherwise, the head assembly 520 can be employed to form connective lesions between the superior and inferior aspects of separately-formed pulmonary vein island lesions as previously described, whereas the secondary ablation electrodes 526a-526c are utilized, with corresponding re-positioning of the contact face 534, to define another portion of the MAZE pattern. Regardless, the auxiliary electrode pairs 528a, 528b and 530a, 530b are operable in manners akin to previous descriptions for performing various pacing and/or sensing operations. Other features described above (e.g., suction regions, liquid supply/cooling, etc.) can optionally be incorporated into the head assembly 520.

Another embodiment head assembly 540 in accordance with principles of the present disclosure and useful with the ablation device 22 (FIG. 1) is shown, in simplified form, in FIG. 11P. The head assembly 540 includes a paddle body 542, primary ablation electrodes 544a, 544b, secondary ablation electrodes 546a, 546b, tertiary ablation electrodes 548a, 548b, and three pairs of auxiliary electrodes 550a-550c. The paddle body 542 is sized and shaped for delivery to the posterior left atrium via a subxiphoid surgical approach, and can have the circular-like shape shown. The electrodes 544a-550c are maintained by, and are exteriorly exposed relative to a contact face 552 of, the paddle body 542 in a spatially fixed manner. The primary electrodes 554a, 554b are arranged in a segmented fashion at a perimeter of the paddle body 542. Thus, the primary ablation electrodes 544a, 544b define a circle-like pattern. The secondary ablation electrodes 546a, 546b are also arranged in a segmented fashion to define a circular-like pattern, but are located within, and spaced from, the primary ablation electrodes 544a, 544b. The tertiary ablation electrodes 548a, 548b are within, and spaced from, the circular pattern of the secondary ablation electrodes 546a, 546b. Finally, the auxiliary electrode pairs 560a-560c are mounted to the paddle body 542 between the circular patterns of the ablation electrodes 544a-548b as shown. Desired lesion patterns can be generated by directing the contact face 552 against targeted epicardial tissue of the posterior left atrium and sequentially energizing respective ones of the ablation electrode 544a-548d. For example, the primary ablation electrodes 544a, 544b can be energized to form a lesion pattern that interconnects superior and inferior aspects of separately-formed pulmonary vein island lesions. The auxiliary electrode pairs 560a-560c are operable in manners akin to those previously described, facilitating various pacing and/or sensing procedures. Other features described above (e.g., suction regions, liquid supply/cooling, etc.) can optionally be incorporated into the head assembly 540.

Figures 11Q, 11R:
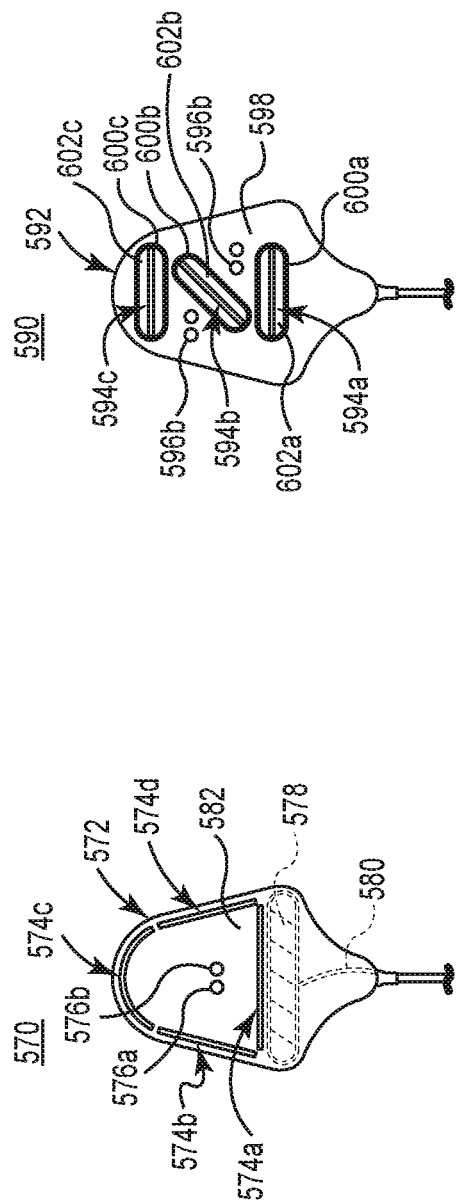

Another embodiment head assembly 570 in accordance with principles of the present disclosure and useful with the ablation device 22 (FIG. 1) is shown, in simplified form, in FIG. 11Q. The head assembly 570 includes a paddle body 572, ablation electrodes 574a-574c, and auxiliary electrodes 576a, 576b. The paddle body 572 is sized and shaped for delivery to the posterior left atrium via a subxiphoid surgical approach, and can have the wedge-like shape shown. In addition, the paddle body 572 forms or defines a cooling zone 578, for example as an internal pocket within the paddle body 572. Tubing 580 is fluidly connected to the cooling zone 578, and serves to deliver a cooling liquid (e.g., saline) to the cooling zone 578. The electrodes 574a-576b are maintained by, and exteriorly exposed relative to a contact face 582 of, the paddle body 572 in a spatially fixed manner. The ablation electrodes 574a-574d are arranged along (and in close proximity to) a perimeter of the paddle body 572. The auxiliary electrodes 576a, 576b are located along the paddle body 572 within a pattern defined by the ablation electrodes 574a-574c. During use, the head assembly 570 is operable in manners akin to those previously described, with the contact face 582 being directed against targeted epicardial tissue of the posterior left atrium between the pulmonary vein junctions. The ablation electrodes 574a-574d are sequentially energized to ablate a desired lesion pattern into contacted tissue. The auxiliary electrodes 576a, 576b facilitate the performance of various pacing and/or sensing procedures. In addition, a cooling liquid can be provided to and/or circulate within the cooling zone 578 as desired to effectuate cooling of contacted anatomy (e.g., the circumflex artery).

Another embodiment head assembly 590 in accordance with principles of the present disclosure and useful with the ablation device 22 (FIG. 1) is shown, in simplified form, in FIG. 11R. The head assembly 590 includes a paddle body 592, ablation electrodes 594a-594c, and two pairs of auxiliary electrodes 596a, 596b. The paddle body 592 is sized and shaped for delivery to the posterior left atrium via a subxiphoid surgical approach, and can have the wedge-like shape shown. The electrodes 594a-596b are maintained by, and are exteriorly exposed relative to a contact face 598 of, the paddle body 592. The ablation electrodes 594a-594c are arranged in the Z-like pattern shown. In this regard, skirts 600a-600c are formed or provided about respective ones of the ablation electrodes 594a-594c, and establish corresponding suction regions 602a-602c. A negative pressure source (not shown) is fluidly connected to each of the suction regions 602a-602c; upon application of negative pressure, tissue otherwise in contact with the skirts 600a-600c is pulled or suctioned into intimate contact with the corresponding ablation electrodes 592a-592c. Thus, operation of the head assembly 590 in performing an ablation procedure is akin to previous descriptions, including the contact face 598 being directed against targeted epicardial tissue of the posterior left atrium between the pulmonary vein junctions. Tissue to be ablated is suctioned into contact with the selected ablation electrode 592a-592c and sequentially ablated. The auxiliary electrode pairs 596a, 596b are operable in manners akin to previous descriptions, and can facilitate various pacing and/or sensing procedures.

The ablation instruments, systems, and methods of the present disclosure provide a marked improvement over previous designs. By promoting ready access to, and ablative contact with, epicardial tissue of the posterior left atrium via a subxiphoid surgical approach, procedures can be performed in ways not heretofore available. The subxiphoid approach is a midline skin incision that avoids the division of major muscle groups or bone. The incision is made inferior to the sternum, such that the extent of the incision is primarily a cosmetic concern and is without limitation from surrounding bone. The surgeon has the choice of how long of an incision to apply in order to achieve proper visibility of the targeted tissue site. The incision may be easily widened using standard and/or long blade retractors. Regardless, a desired portion of a MAZE lesion pattern is easily formed with the ablation instrument of the present disclosure, forming desired posterior aspect pulmonary vein island lesion interconnections. Further, in some embodiments, a so-formed conduction block can be readily evaluated with the ablation instrument.

Although the present disclosure has been described with reference to preferred embodiments, workers skilled in the art will recognize that changes can be made in form and detail without departing from the spirit and scope of the present disclosure.

What is claimed is:

1. An ablation instrument for applying ablative energy to tissue, the ablation instrument comprising:
   a head assembly defining a tissue contact face and including:
   first and second ablation electrodes exteriorly exposed at the tissue contact face;
   a first skirt originating and projecting from the tissue contact face in a direction away from the first ablation electrode and completely surrounding a perimeter of the first ablation electrode to define a first suction region;
   a second skirt originating and projecting from the tissue contact face in a direction away from the second ablation electrode and completely surrounding a perimeter of the second ablation electrode to establish a second suction region; wherein the second skirt does not surround the first suction region and the first skirt does not surround the second suction region;
   a first suction aperture formed by the tissue contact face within the first suction region for applying a suction force to the first suction region; and
   a second suction aperture formed by the tissue contact face within the second suction region for applying a suction force to the second suction region.

2. The ablation instrument of claim 1, wherein the instrument is manipulable to locate the tissue contact face on epicardial tissue between left and right pulmonary vein junctions of a patient's posterior left atrium via a subxiphoid surgical approach.

3. The ablation instrument of claim 1, wherein the instrument is manipulable to locate the first and second ablation electrodes on epicardial tissue between left and right pulmonary vein junctions of a patient's posterior left atrium via a subxiphoid surgical approach.

4. The ablation instrument of claim 1, further comprising:
   a tubular member extending from the head assembly.

5. The ablation instrument of claim 4, wherein a maximum diameter of the tubular member is less than a maximum width of the head assembly.

6. The ablation instrument of claim 4, wherein the first and second ablation electrodes are arranged to extend generally perpendicular to a central axis of the tubular member.

7. The ablation instrument of claim 4, further comprising:
   one or more suction lumens fluidly connected to each of the suction apertures and extending through the tubular member.

8. The ablation instrument of claim 4, further comprising:
   wiring electrically connected to the first and second ablation electrodes for delivering energy to the first and second ablation electrodes, the wiring extending through the tubular member.

9. The ablation instrument of claim 1, further comprising:
   a negative pressure source fluidly connected to the suction apertures via one or more suction lumens.

10. The ablation instrument of claim 1, wherein the first and second ablation electrodes are configured such that when the head assembly is positioned along the posterior left atrium between left and right pulmonary veins, the ablation electrodes are operable to form lesions interconnecting island lesions surrounding junctions of the pulmonary veins with the left atrium.

11. The ablation instrument of claim 1, wherein the head assembly further includes:
   first and second auxiliary electrodes exteriorly exposed at the contact face, wherein the auxiliary electrodes are electrically isolated from one another and are located between the first and second ablation electrodes.

12. The ablation instrument of claim 11, wherein the auxiliary electrodes are operable to perform a pacing operation on a patient's heart.

13. The ablation instrument of claim 11, wherein the auxiliary electrodes are operable to sense electrical activity on a patient's heart.

14. The ablation instrument of claim 1, wherein the first ablation electrode and the second ablation electrode do not share an axis transverse to a longitudinal axis of the instrument.

15. The ablation instrument of claim 1, wherein the head assembly includes fingers configured to receive and support a segment of the first ablation electrode.

16. The ablation instrument of claim 15, wherein the fingers are configured to frictionally retain the first ablation electrode.

17. The ablation instrument of claim 1, wherein the first skirt is compliant.

18. The ablation instrument of claim 1 wherein the second electrode has a curve extending between opposing longitudinal ends of the second electrode.

* * * * *